US009918674B2

(12) United States Patent
Bogdanovich et al.

(10) Patent No.: US 9,918,674 B2
(45) Date of Patent: Mar. 20, 2018

(54) GARMENT SYSTEM WITH ELECTRONIC COMPONENTS AND ASSOCIATED METHODS

(71) Applicants: Phillip Bogdanovich, Austin, TX (US); Craig Weller, Austin, TX (US)

(72) Inventors: Phillip Bogdanovich, Austin, TX (US); Craig Weller, Austin, TX (US)

( * ) Notice: Subject to any disclaimer, the term of this patent is extended or adjusted under 35 U.S.C. 154(b) by 0 days.

(21) Appl. No.: 15/431,495

(22) Filed: Feb. 13, 2017

(65) Prior Publication Data

US 2017/0281055 A1 Oct. 5, 2017

Related U.S. Application Data

(63) Continuation of application No. 14/931,545, filed on Nov. 3, 2015, now Pat. No. 9,566,033.

(Continued)

(51) Int. Cl.
*G08C 19/22* (2006.01)
*H04Q 9/00* (2006.01)
(Continued)

(52) U.S. Cl.
CPC .......... *A61B 5/6804* (2013.01); *A61B 5/0002* (2013.01); *A61B 5/0205* (2013.01);
(Continued)

(58) Field of Classification Search
CPC ... A61B 5/0022; A61B 5/0205; A61B 5/0816; A61B 5/1112; A61B 5/1118; A61B 5/14542; A61B 2560/0214; A61B 2560/0242; A61B 2560/0412; A61B 5/0002; A61B 5/0024; A61B 5/021; A61B 5/02438; A61B 5/1117; A61B 5/14532; A61B 5/4806; A61B 5/742;
(Continued)

(56) References Cited

U.S. PATENT DOCUMENTS

2012/0139731 A1* 6/2012 Razoumov ........... A61B 5/0022
340/573.1
2012/0188083 A1* 7/2012 Miller, II ............... A42B 3/046
340/573.1

(Continued)

*Primary Examiner* — Emily C Terrell
(74) *Attorney, Agent, or Firm* — Meyertons, Hood, Kivlin, Kowert & Goetzel, P.C.; Gareth M. Sampson

(57) ABSTRACT

The disclosure provides a wireless biometric monitoring system that may be capable of acquiring, compiling, analyzing, and transmitting biometric data in near real time/real time. The system may utilize either the most up-to-date Bluetooth protocol (currently Bluetooth Smart) or a similar wireless protocol. The system may further integrate through this wireless protocol with peripheral devices to expand the measurement capacity of the system.

In embodiments, the system may be capable of monitoring multiple biometric responses including, but not limited to: skin temperature, core temperature, respirations, heart rate, predicted tidal volume, chest wall movement, abdominal movement in conjunction with inspiration, abdominal movement in conjunction with expiration, HRR (heart rate reserve), HRV (heart rate variability), body position relevant to perpendicular, shoulder position relevant to hip position, general body posture, up time, down time, and malfunctions.

19 Claims, 18 Drawing Sheets

Related U.S. Application Data

(60) Provisional application No. 62/074,521, filed on Nov. 3, 2014.

(51) Int. Cl.
  *G08B 1/08* (2006.01)
  *A61B 5/00* (2006.01)
  *A61B 5/0205* (2006.01)
  *A61B 5/11* (2006.01)
  *A61B 5/08* (2006.01)

(52) U.S. Cl.
  CPC ............ *A61B 5/0816* (2013.01); *A61B 5/1112* (2013.01); *A61B 5/1116* (2013.01)

(58) Field of Classification Search
  CPC ............ A61B 2503/10; A61B 2505/03; A61B 2560/0233; A61B 2560/0285; A61B 2560/0456; A61B 2562/0204; A61B 2562/08; A61B 2562/166; A61B 5/0006; A61B 5/0008; A61B 5/0026; A61B 5/01; A61B 5/02055; A61B 5/0215; A61B 5/022; A61B 5/024; A61B 5/0402; A61B 5/1114; A61B 5/112; A61B 5/1122; A61B 5/1128; A61B 5/14551; A61B 5/201; A61B 5/22; A61B 5/411; A61B 5/4818; A61B 5/4866; A61B 5/4875; A61B 5/6831; A61B 5/6833; A61B 5/721; A61B 5/7214; A61B 5/7225; A61B 5/7242; A61B 5/7257; A61B 5/726; A61B 5/7267; A61B 5/7275; A61B 5/743; A61B 5/7455; A61B 5/7465; A61B 5/7475; A61B 7/003; A61B 8/02; A61B 8/06; A61B 8/488; A61B 8/565; A61B 5/0476; A61B 5/0488; A61B 5/0492; A61B 5/1113; A63B 2208/12; A63B 2220/30; A63B 2220/40; A63B 2225/50; A63B 24/00; A63B 69/0028; A63B 69/004; A63B 69/16; A63B 69/26; H04L 67/22
  USPC .............. 340/870.07, 870.11, 539.11–539.13
  See application file for complete search history.

(56) References Cited

U.S. PATENT DOCUMENTS

2012/0246795 A1\* 10/2012 Scheffler ................ A41D 1/002
  2/69
2014/0070957 A1\* 3/2014 Longinotti-Buitoni A61B 5/02055
  340/870.01

\* cited by examiner

GARMENT SYSTEM WITH ELECTRONIC COMPONENTS AND ASSOCIATED METHODS

CROSS-REFERENCE TO RELATED APPLICATIONS

This application claims priority to Provisional Patent Application No. 62/074,521, filed Nov. 3, 2014, which is hereby incorporated by reference in its entirety.

FIELD OF THE INVENTION

The present disclosure relates to a garment, more specifically a garment system with electronic components for monitoring biometric functionality.

BACKGROUND OF THE INVENTION

The wearable technology sector has recently gained a vast amount of interest from individual and companies alike. Devices such as wristbands, glasses, and watches may function to gather biometric data from an individual's body such as heart rate, force on a body, acceleration of a body, etc. A multi-faceted garment wearable incorporating a plurality of biometric analytical devices has not been successfully created.

The disclosed subject matter provides a wireless biometric monitoring system that may be capable of acquiring, compiling, analyzing, and transmitting biometric data in near real time/real time. The system may utilize either the most up-to-date Bluetooth protocol (currently Bluetooth Smart) or a similar wireless protocol. The system may further integrate through this wireless protocol with peripheral devices to expand the measurement capacity of the system.

BRIEF SUMMARY OF THE INVENTION

The disclosure provides a wireless biometric monitoring garment system that may be capable of acquiring, compiling, analyzing, and transmitting biometric data in near real time/real time. The system may utilize either the most up-to-date Bluetooth protocol (currently Bluetooth Smart) or a similar wireless protocol. The system may further integrate through this wireless protocol with peripheral devices to expand the measurement capacity of the system.

The system may be capable of monitoring multiple biometric responses including, but not limited to: skin temperature, core temperature, respirations, heart rate, predicted tidal volume, chest wall movement, abdominal movement in conjunction with inspiration, abdominal movement in conjunction with expiration, HRR (heart rate reserve), HRV (heart rate variability), body position relevant to perpendicular, shoulder position relevant to hip position, general body posture, up time, down time, and malfunctions.

The system may be capable of monitoring multiple biometric peripheral processes through Bluetooth Smart including, but not limited to: DTR, eye movement, eye position, reflex velocity, visual tracking, visual focal points, tactile response, and skin conductivity.

In certain embodiments, the system may be a shirt. The shirt may be constructed of a quick dry material with antistatic and anti-microbial properties. The shirt may be form fitting (Athletic fit) comprised of a polymer mix with elastic fiber similar to spandex.

In certain embodiments, the garment system may be made available in a number of sizes similar to but not relegated to standard American sizing. The garment system may be available in full and half sizes ranging from 3 to 8. A 3 may be the equivalent of an extra extra small and an 8 may be similar to an extra extra extra large. In order to accurately measure the physiological responses, the garment system may be form fitting and snug to provide close contact with the skin; hence the 11 available sizes.

The characteristics of the garment may ensure that the garment may have access to and control over an individual's biometric data in the most intuitive and dynamic way possible without having to be relegated to a lab.

BRIEF DESCRIPTION OF THE DRAWINGS

The novel features believed characteristic of the disclosed subject matter will be set forth in any claims that are filed later. The disclosed subject matter itself, however, as well as a preferred mode of use, further objectives, and advantages thereof, will best be understood by reference to the following detailed description of an illustrative embodiment when read in conjunction with the accompanying drawings, wherein:

DETAILED DESCRIPTION OF ILLUSTRATIVE EMBODIMENTS

Figure 1:
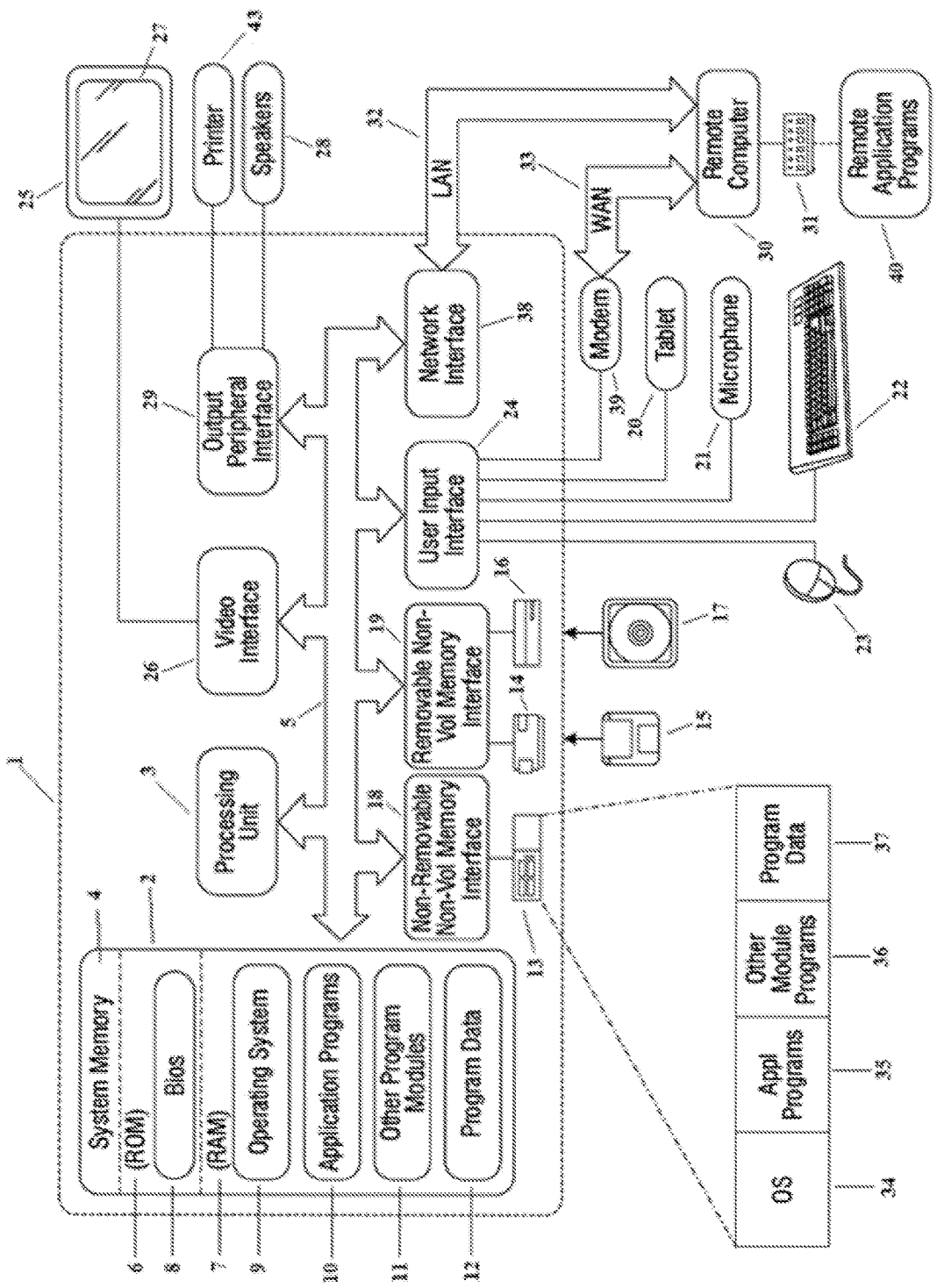
FIG. 1 displays a computing system and related peripherals that may operate with the garment system with electronic components in accordance with embodiments.

Reference now should be made to the drawings, in which the same reference numbers are used throughout the different figures to designate the same components.

It will be understood that, although the terms first, second, third, etc. may be used herein to describe various elements, these elements should not be limited by these terms. These terms are only used to distinguish one element from another element. Thus, a first element discussed below could be termed a second element without departing from the teachings of the present disclosure.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although described with reference to personal computers and the Internet, one skilled in the art could apply the principles discussed herein to any computing or mobile computing environment. Further, one skilled in the art could apply the principles discussed herein to communication mediums beyond the Internet.

It will be appreciated that for simplicity and clarity of illustration, where considered appropriate, reference numerals may be repeated among the figures to indicate corresponding or analogous elements. In addition, numerous specific details are set forth in order to provide a thorough understanding of the implementations described herein. However, it will be understood by those of ordinary skill in the art that the implementations described herein may be practiced without these specific details. In other instances, well-known methods, procedures and components have not been described in detail so as not to obscure the implementations described herein. Also, the description is not to be considered as limiting the scope of the implementations described herein.

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, electrical and other changes may be made without departing from the scope of the implementations. The following detailed description is, therefore, not to be taken in a limiting sense.

With reference to FIG. 1, an exemplary system within a computing environment for implementing the disclosure includes a general purpose computing device in the form of a computing system 1, commercially available from, for example, Intel, IBM, AMD, Motorola, Cyrix, etc. Components of the computing system 2 may include, but are not limited to, a processing unit 3, a system memory 4, and a system bus 5 that couples various system components including the system memory 4 to the processing unit 3. The system bus 5 may be any of several types of bus structures including a memory bus or memory controller, a peripheral bus, or a local bus using any of a variety of bus architectures.

Computing system 1 typically includes a variety of computer readable media. Computer readable media can be any available media that can be accessed by the computing system 1 and includes both volatile and nonvolatile media, and removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data.

Computer memory includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the computing system 1.

The system memory 4 includes computer storage media in the form of volatile and/or nonvolatile memory such as read only memory (ROM) 6 and random access memory (RAM) 7. A basic input/output system (BIOS) 8, containing the basic routines that help to transfer information between elements within computing system 1, such as during start-up, is typically stored in ROM 6. RAM 7 typically contains data and/or program modules that are immediately accessible to and/or presently being operated on by processing unit 3. By way of example, and not limitation, an operating system 9, application programs 10, other program modules 11, and program data 12 are shown.

Computing system 1 may also include other removable/non-removable, volatile/nonvolatile computer storage media. By way of example only, a hard disk drive 13 that reads from or writes to non-removable, nonvolatile magnetic media, a magnetic disk drive 14 that reads from or writes to a removable, nonvolatile magnetic disk 15, and an optical disk drive 16 that reads from or writes to a removable, nonvolatile optical disk 17 such as a CD ROM or other optical media could be employed to store the invention of the present embodiment. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 13 is typically connected to the system bus 5 through a non-removable memory interface such as interface 18, and magnetic disk drive 14 and optical disk drive 16 are typically connected to the system bus 5 by a removable memory interface, such as interface 19.

The drives and their associated computer storage media, discussed above, provide storage of computer readable instructions, data structures, program modules and other data for the computing system 1. For example, hard disk drive 13 is illustrated as storing operating system 34, application programs 35, other program modules 36, and program data 37. Note that these components can either be the same as or different from operating system 9, application programs 10, other program modules 11, and program data 12. Operating system 34, application programs 35, other program modules 36, and program data 37 are given different numbers here to illustrate that, at a minimum, they are different copies.

A user may enter commands and information into the computing system 1 through input devices such as a tablet, or electronic digitizer, 20, a microphone 21, a keyboard 22, and pointing device 23, commonly referred to as a mouse, trackball, or touch pad. These and other input devices are often connected to the processing unit 3 through a user input interface 24 that is coupled to the system bus 5, but may be connected by other interface and bus structures, such as a parallel port, game port or a universal serial bus (USB).

A monitor 25 or other type of display device is also connected to the system bus 5 via an interface, such as a video interface 26. The monitor 25 may also be integrated with a touch-screen panel 27 or the like. Note that the monitor and/or touch screen panel can be physically coupled to a housing in which the computing system 1 is incorporated, such as in a tablet-type personal computer. In addition, computers such as the computing system 1 may also include other peripheral output devices such as speakers 28 and printer 43, which may be connected through an output peripheral interface 29 or the like.

Computing system 1 may operate in a networked environment using logical connections to one or more remote computers, such as a remote computing system 30. The remote computing system 30 may be a personal computer (including, but not limited to, mobile electronic devices), a server, a router, a network PC, a peer device or other common network node, and typically includes many or all of the elements described above relative to the computing system 1, although only a memory storage device 31 has been illustrated. The logical connections depicted include a local area network (LAN) 32 connecting through network interface 38 and a wide area network (WAN) 33 connecting via modem 39, but may also include other networks. Such networking environments are commonplace in offices, enterprise-wide computer networks, intranets, and the Internet.

For example, in the present embodiment, the computer system 1 may comprise the source machine from which data is being generated/transmitted and the remote computing system 30 may comprise the destination machine. Note however that source and destination machines need not be connected by a network or any other means, but instead, data may be transferred via any media capable of being written by the source platform and read by the destination platform or platforms.

In another example, in the present embodiment, the remote computing system 30 may comprise the source machine from which data is being generated/transmitted and the computer system 1 may comprise the destination machine.

In a further embodiment, in the present disclosure, the computing system 1 may comprise both a source machine from which data is being generated/transmitted and a destination machine and the remote computing system 30 may also comprise both a source machine from which data is being generated/transmitted and a destination machine.

Referring to FIG. 1, for the purposes of this disclosure, it will be appreciated that remote computer 30 may include any suitable terms such as, but not limited to "device", "processor based mobile device", "mobile device", "electronic device", "processor based mobile electronic device", "mobile electronic device", "wireless electronic device", "location-capable wireless device," and "remote device" including a smart phone or tablet computer.

The central processor operating pursuant to operating system software such as, but not limited to Apple IOS®), Google Android®, IBM OS/2®, Linux®, UNIX®, Microsoft Windows®, Apple Mac OSX®, and other commercially available operating systems provides functionality for the services provided by the present invention. The operating system or systems may reside at a central location or distributed locations (i.e., mirrored or standalone).

Software programs or modules instruct the operating systems to perform tasks such as, but not limited to, facilitating client requests, system maintenance, security, data storage, data backup, data mining, document/report generation, and algorithm generation. The provided functionality may be embodied directly in hardware, in a software module executed by a processor, or in any combination of the two.

Furthermore, software operations may be executed, in part or wholly, by one or more servers or a client's system, via hardware, software module, or any combination of the two. A software module (program or executable) may reside in RAM memory, flash memory, ROM memory, EPROM memory, EEPROM memory, registers, hard disk, a removable disk, a CD-ROM, DVD, optical disk, or any other form of storage medium known in the art. An exemplary storage medium is coupled to the processor such that the processor can read information from, and write information to, the storage medium. In the alternative, the storage medium may be integral to the processor. The processor and the storage medium may also reside in an application specific integrated circuit (ASIC). The bus may be an optical or conventional bus operating pursuant to various protocols that are well known in the art.

All methods described herein can be performed in a suitable order unless otherwise indicated herein or otherwise clearly contradicted by context. The use of any and all examples, or exemplary language (e.g., "such as"), is intended merely to better illustrate the disclosure and does not pose a limitation on the scope of the disclosure unless otherwise claimed. No language in the specification should be construed as indicating any non-claimed element as essential to the practice of the disclosure as used herein.

The detailed description set forth herein in connection with the appended drawings is intended as a description of exemplary embodiments in which the presently disclosed apparatus and system can be practiced. The term "exemplary" used throughout this description means "serving as an example, instance, or illustration," and should not necessarily be construed as preferred or advantageous over other embodiments.

Figure 2A:
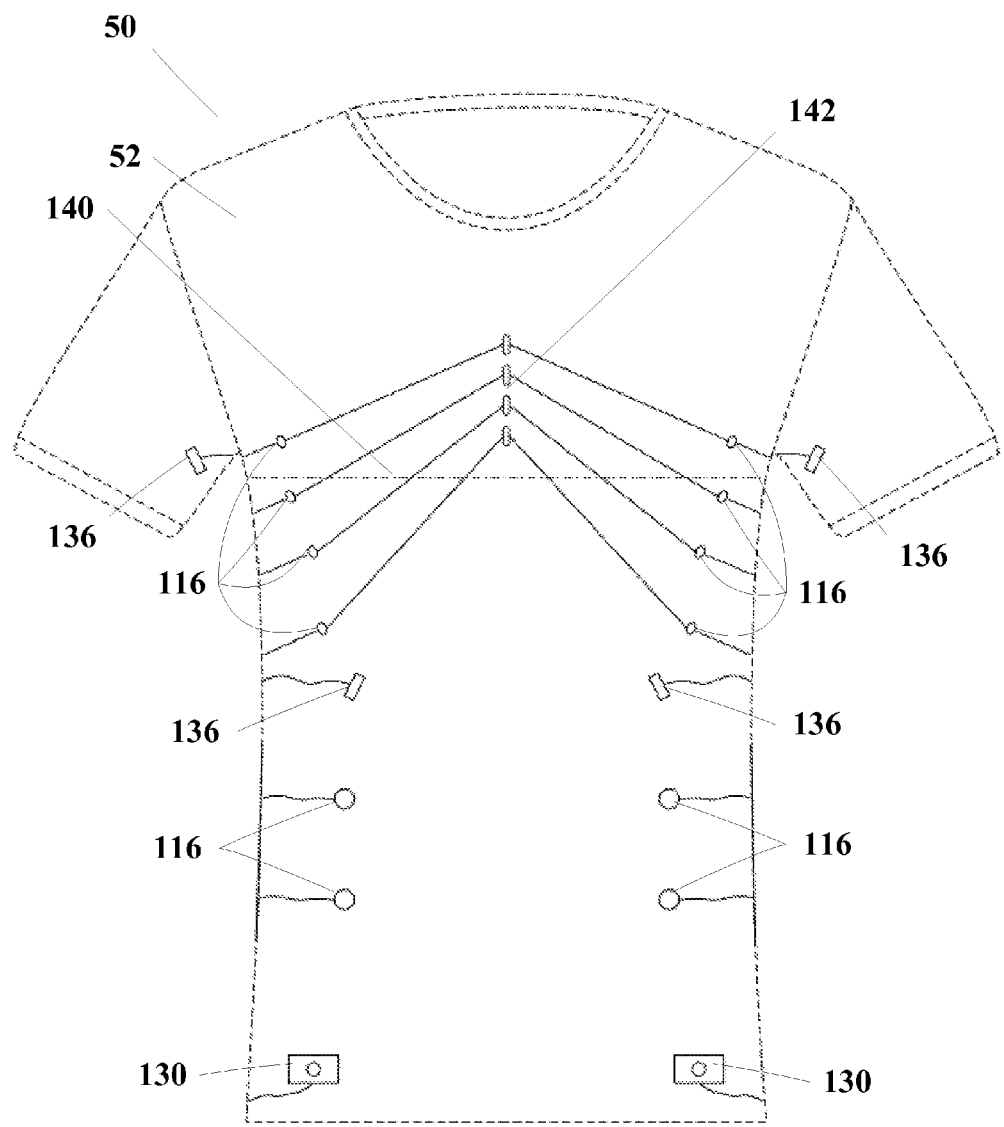
FIG. 2A displays one embodiment of the anterior view of a garment system showing various components found within the garment.
Figure 2B:
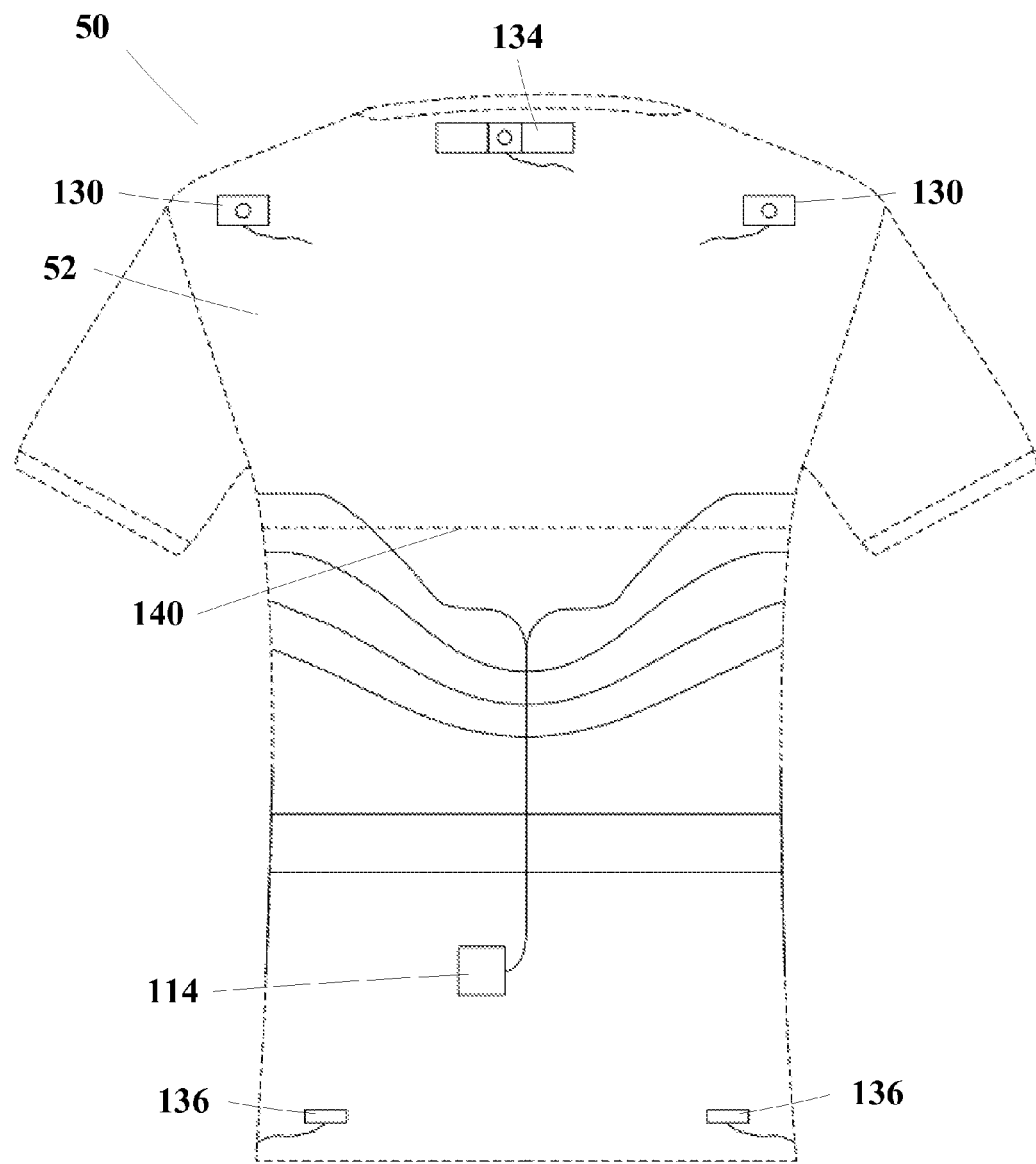
FIG. 2B displays one embodiment of the posterior view of a garment system showing various components found within the garment.

FIG. 2A displays one embodiment of the anterior view of a garment system 50 showing various components found within the garment 50. FIG. 2B displays one embodiment of the posterior view of a garment system 50 showing various components found within the garment 50. At least a portion of the garment 50 may be constructed of a quick dry material with antistatic and anti-microbial properties. The garment 50 may be form fitting (athletic fit) comprised of a plurality of fabric layers and including elastic fibers similar to spandex. The garment body 52 may be the main body of the system 50 that may house a number of electronic components either within or on the garment structure. In embodiments, the garment 50 may be made of a quick dry elastic polymer blend that may provide support to the wearer, welded non-chafing seams, and a stable platform for biometric sensors, GPS, and processors from which to operate. The garment fit may be athletic, similar to, in embodiments, an undershirt worn by a soldier or professional football player. In embodiments, the garment 50 may include fabric enhancements including better moisture wicking, thermal management, and muscle group support.

The garment 50 may be made available in a number of sizes similar to but not relegated to standard American sizing. The garment 50 may be available in full and half sizes ranging from 3 to 8. In embodiments, a 3 may be the equivalent of an extra extra small and an 8 may be similar to an extra extra extra large. In order to accurately measure the physiological responses, the garment 50 may be form fitting and snug. Hence, in embodiments, 11 available sizes may be provided.

In embodiments, the garment 50 may be unisex. Because the garment 50, in embodiments, may be fitted based on torso length relevant to chest wall circumference and the unit is also constructed from an elastic material, the garment 50 may be unisex. This may make manufacturing, shirt selection, distribution, and inventory management more manageable.

In embodiments, the garment 50 may be form fitting and may be designed to be worn for prolonged periods of time. The garment 50 may be designed to fit and feel like a typical athletic garment. Under normal circumstances, the garment 50 may not require special fitting. The garment 50 being form-fitting may allow the garment 50 to properly collect data from an individual. In embodiments, a sizing chart may be provided to an individual with the garment 50 to recommend shirt sizes that may correspond with chest measurements in embodiments in which the garment 50 is a shirt. The process may be similar to effectively fitting an individual for a high-end backpack or daypack, which is a practice common in the outdoor sports retail space. Under unique circumstances, the garment 50 may be worn under other equipment for prolonged periods of time (such as football pads) or the wearer may have a unique body shape fitting specific to the individual, in which case a specially made garment 50 may be created.

In embodiments, a garment system 50 may include eight primary components: a garment body 52, a heart rate monitor (not shown), a plurality of respiration/skeletal position monitors 116, a plurality of accelerometers 130, a GPS/WWAN component 134, a processor 114, a cellular/satellite transceiver (not shown), a low frequency receiver/transceiver system (not shown), a dashboard application, and a kinetic power module 138 and generators 136. Wiring for at least some of the components, in embodiments, may be displayed in FIGS. 2A and 2B.

In embodiments, at least one of the cellular/satellite transceivers and the low frequency receiver/transceiver system may be housed within the processor 114. In embodiments, at least one of the cellular/satellite transceivers and the low frequency receive/transceiver system may be housed within the garment 50 separate of the processor 114.

In embodiments, the GPS/WWAN component 134 may include at least one of the cellular/satellite transceivers and the low frequency receiver/transceiver system.

In embodiments, the garment 50 may incorporate a Bluetooth Smart Heart Rate Monitor (HR) that may function utilizing decoding algorithms and three lead ekg equivalent monitoring straps. The HR monitor may stream pulse rate to the garment's processor 114 which may run the data through multiple algorithms developed and offered as a package. The algorithms offered may offer, but is not limited to, the following outputs: BPM, HRR (heart rate reserve), stress response, and HRV (heart rate variability).

In embodiments, the garment heart rate monitor may be integrated into the garment material. In embodiments, the monitor may utilize three lead EKG equivalent monitoring techniques using electrically conductive pads. The heart rate monitor (not shown) may be positioned anatomically under the breast line and over the top of the xiphoid process (in proximity to dotted line 140 found in FIG. 2A). The monitor may track pulse rate in near real-time and may transmit the information via hardwire to the processor 114 incorporated into the garment 50. The heart rate monitor may also include low-frequency wireless technology such as, but not limited to Bluetooth Smart. The Bluetooth Smart or similar technology may allow for the heart rate to be transmitted in near real-time to a third-party device, such as, but not limited to an electronic device including an application. This transmission may be secondary to the hardwired connection to the processor 114. The contact pads for the heart rate monitor may be rubberized and fully encapsulated to ensure that the unit is watertight. The battery 132 for the heart rate monitor may be incorporated into the base of the garment 50 and may be connected to the heart rate monitor via a wired connection. In embodiments, the heart rate monitor may include updated firmware and technology upgrades including more efficient monitoring, three-dimensional sonography, target specific ultrasound, and more frequent data transmissions.

In embodiments, the heart rate monitor may be a standard heart rate monitor that is meant to circumnavigate either a portion of the chest or a portion adjacent the chest.

In embodiments, the garment 50 may comprise a Bluetooth Smart or other similar low frequency wireless technology which may allow for the incorporation of 3rd party monitoring tools such as, but not limited to: deep tendon reflex monitoring cuffs, pedometers, glasses utilized to track multiple periods of vision, eye movement, and focal points, skin conductivity monitors, skin temp monitors, and atmospheric monitors.

In embodiments, the garment 50 may incorporate an onboard processor 114 allowing for the processing of all information acquired through the various sensors. This means that there may be a temporary break in connectivity information that may still be processed and stored for a burst transition when uplink is re-established.

In embodiments, the garment 50 may incorporate a wireless mobile data uplink including satellite data for military use. This may allow for the transmission of information over cellular or satellite data protocol in the event that another network system isn't available.

In embodiments, the garment 50 may be wirelessly accessible through a proprietary mobile and web application (alternatively referred to as a module). The application paired with the garment 50 may allow for the simultaneous review of all biometric information as well as complementary information generated by the algorithmic manipulation of procured data. The application may allow for the same review as the app but through a universally accessible web platform. This combination of review systems may allow for the management, utilization, and near real-time review of gathered data regardless of the physical location of the assessor relevant to the wearer of the garment 50.

The garment 50 application may be, in embodiments, a native iOS and Android application as well as a web platform. The dashboard may access the garment server through a secure Internet connection. The passing of information and system management may occur through a garment web portal across a garment server. This setup may allow for wireless firmware updates and remote diagnostic capabilities. Live "over-the-wire" firmware updates may occur as enhancements are made and the garment application may be updated as improvements occur. Initially, the garment application may allow for the measurement and viewing of all biometric processes being monitored and GPS location. In embodiments, the garment 50 may include control capabilities such as VO2 Threshold, Tidal Volume, WAN locating, 3D Thoracic wall movement diagramming, third-party apps, etc.

In embodiments, the garment 50 may include integrated cellular and/or satellite transceivers and receiver sets. The purpose may be to allow the streaming of information from the garment processor 114 to the garment associated website to be reflected in the dashboard/application of authorized viewers. This technology may allow for global access to GPS data as well as biometric feedback processes. For military users, a satellite receiver/transceiver may be integrated into the garment 50. Although more expensive, data transmitted over satellite uplink may be more reliable in non-permissive environments. The antennas for either the satellite or cellular unit may be a flat integrated antenna that may be flexible and sewn along the top line of the garment 50. In embodiments, the garment 50 may include smaller cellular and/or satellite circuit board integration, lighter weight materials, smaller antennas, and faster data transfer rates.

In embodiments, the garment 50 may utilize industry-leading low-frequency transmitter/receiver systems to create an ecosystem around the garment 50. One embodiment may incorporate a low-frequency system such as Bluetooth Smart. This technology may allow for the addition of third-party hardware for extended biofeedback response capabilities. Some of the hardware concepts may include glasses to track movement and pupil dilation, wristbands to monitor skin conductivity and temperature, ambient temperature sensors, and DTR monitoring. In embodiments, the garment 50 may include the most up-to-date low-frequency wirelessly integrated technology. This may include smaller transmitters and receivers that may move larger quantities of data and smaller package sizes over greater distances. The protocols may be expanded to include a wider variety of third-party hardware. In further embodiments, iterations of submersible technology may be incorporated.

In embodiments, the garment 50 may incorporate a magnetic respiratory monitor that may measure chest wall and abdominal movement. In embodiments, the respiratory monitor may measure chest wall and abdominal movement at twelve points on the body, with six points being on a first side of the body and six points being on a second side of the body. Four leads may be placed at relevant points along the thoracic wall to monitor the linear movement of the related space along a linear plane. Two leads may be placed on the lateral aspect of the abdominal wall to monitor for diaphragmatic breathing. The respiration rate, frequency, and depth may be transmitted over wire in real-time to the garment's onboard processor 114 where the information may be processed through a series of algorithms to determine results such as, but are not limited to, the following: respiration depth, respiration quality, respiration rate, respiratory rhythm, and relevant chest wall and abdominal movement (symmetric, asymmetric, variance, etc.).

Figure 3:
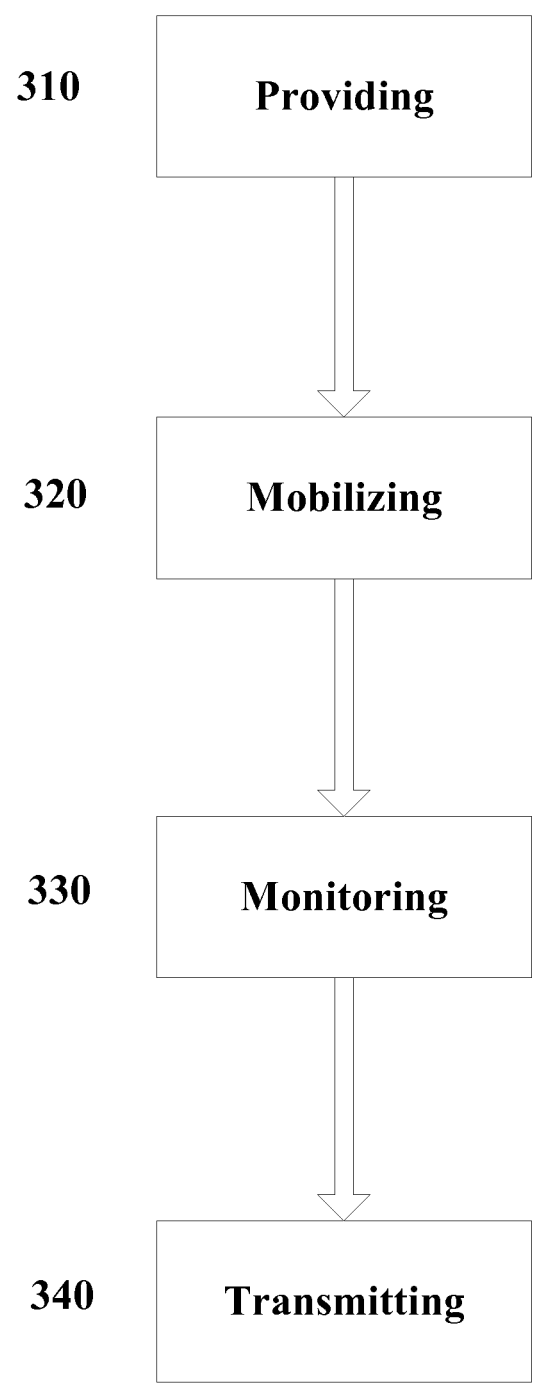
FIG. 3 displays a method for monitoring an individual using a magnetic respiratory monitor in accordance with embodiments.

FIG. 3 displays a method 300 for monitoring an individual using a magnetic respiratory monitor in accordance with embodiments. Method 300 may include providing 310 a pair of magnets. In embodiments, a magnet may be static. A second magnet may be mobilized 320 in the vicinity of the static magnet. A magnetometer may then monitor 330 the variation in magnetic force applied to the static magnet by a mobile magnet attached to the mediastinal breastplate of the garment 50, the position 142 of which may be found in FIG. 2A depicted as a dotted line. Magnetic variance may occur on inspiration and expiration as the magnet attached to the breast plate moves away from the static magnet during inspiration and back towards the static magnet during expiration. The variance in force may be transmitted 340 by the magnetometer to the processor. The number of times the variances are recorded over a period of time may be identified as the number of respirations in that period. The pair of magnets involved in this process may be encapsulated in a thin waterproof tube in conjunction with the magnetometer. The static magnet may be glued in place to the interior of the watertight tube. Each magnetic device may consist of a magnetometer, a static magnet secured to the interior of the tube, a mobile magnet inserted into the interior of the tube, a watertight tube, and a cable attachment to the breast plate. There may be a plurality, such as, but not limited to, twelve, of these devices distributed throughout the garment 50. In embodiments, four devices may be located over the left lateral aspect of the thorax and four devices may be located over the right lateral aspect of the thorax. In embodiments, two devices may be located over the left anterolateral aspect of the abdomen and two devices may be located over the right anterolateral aspect of the abdomen. In embodiments, a magnetic respiratory monitor may be placed within the garment 50 on each side of the garment 50 correlating with an upper chest wall of an individual so that breathing patterns in these two areas may be monitored. In embodiments, the length of the tube may align with an outward axis of breathing of the individual so that the magnets may move along this axis and provide useful measurable results. In embodiments, the garment 50 may include magnetometry that does not require actual moving magnets, smaller integrated systems, and faster, more reliable reads.

In embodiments, the magnetometer may comprise standard magnetometer components that may be capable of measuring at least one of the following: the magnetization of a magnetic material and the strength and/or direction of a magnetic field at a point in space. In embodiments, a sensor of the magnetometer may be positioned within the magnetic field found within or in the vicinity of the tube housing the static magnet and the mobile magnet.

In embodiments, the garment 50 may be worn in conjunction with a belt. The belt itself may include a magnet and magnetometer setup as previously described with the tube aligning along an axis perpendicular to the length and width of the belt. The belt may, when the garment 50 is worn by an individual, circumnavigate the pelvic region of an individual and may carry out at least one of two tasks: keep a garment 50 in place if an individual is wearing a garment 50 and measuring the pelvic positioning of an individual. In embodiments, the belt may be positioned over the iliac crests of the pelvis.

In embodiments, a garment 50 in the form of a shirt may comprise a waistband sewn within a hem of a shirt. The waistband may, when the garment 50 is worn by an individual, circumnavigate the pelvic region of an individual. The waistband may comprise a magnet and magnetometer setup as previously described with the tube aligning along an axis perpendicular to the length and width of the waistband. The waistband may measure the pelvic positioning of an individual when the individual is wearing a garment 50 including the waistband. In embodiments, the waistband may comprise an elastic material. In embodiments, the belt may be positioned over the iliac crests of the pelvis.

Figure 4:
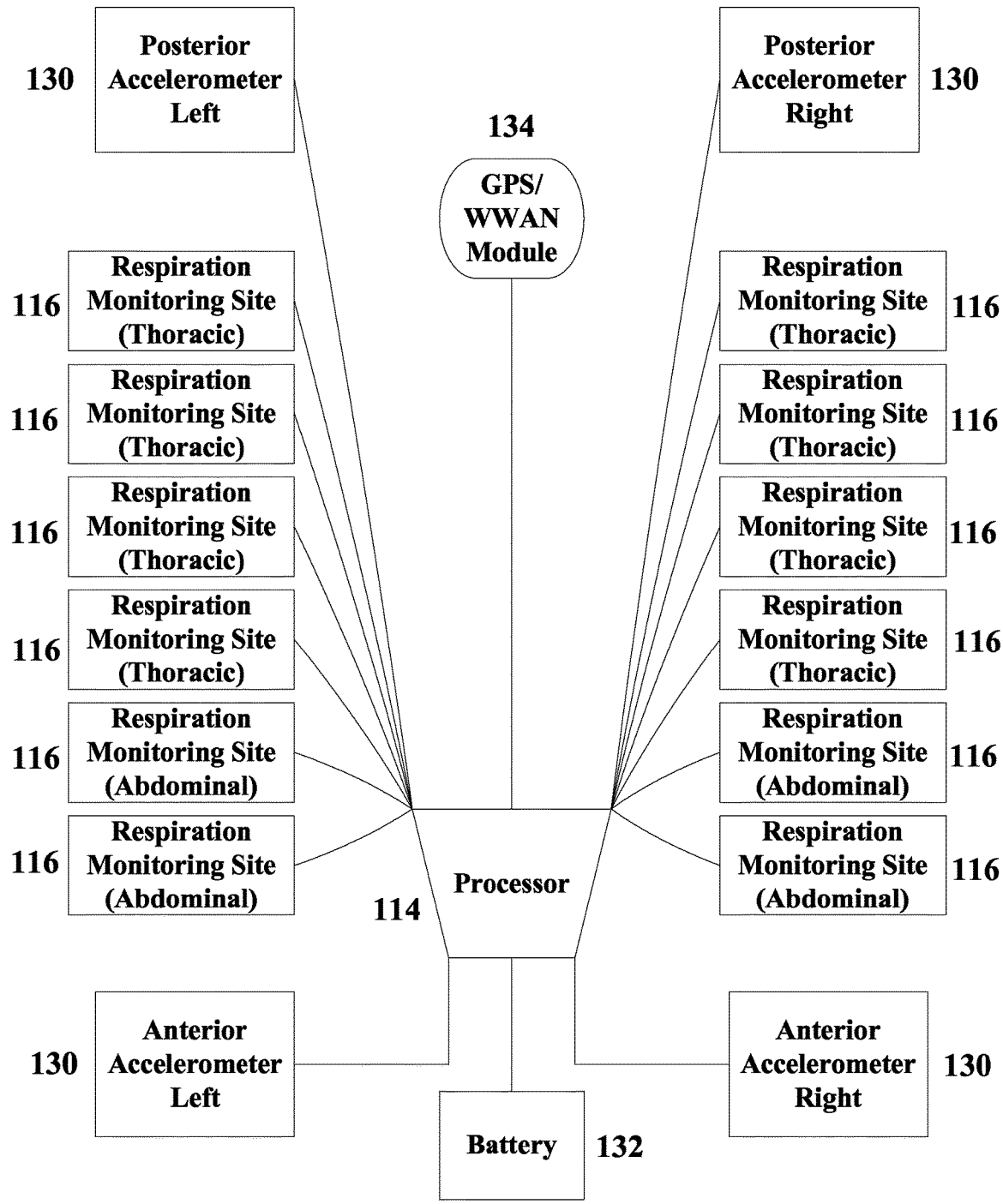
FIG. 4 displays a diagram depicting one embodiment of a wired framework of the garment system.

FIG. 4 displays a diagram depicting one embodiment of a wired framework of the garment system 50. In certain embodiments, the garment 50 may integrate up to twelve primary components.

In embodiments, the garment 50 may comprise an integrated processor 114. Information generated by biometric sensors, Bluetooth extensions, GPS signals, and any other general feedback provided through the garment system 50 may be processed within the garment 50 using the processor 114. Processed data packets may be transmitted via uplink to a server associated with the garment 50 and then made available in near real-time to a dashboard/application; application users may be intended to have access to this information. The mechanism of processing information on board the garment 50 may allow for the continuous cycling and evaluation of data even in the event of uplink loss. This may be critical in high-conflict areas such as areas near powerlines or around dense foliage or building cover. Once communication with the server is re-established, burst transmissions may occur in order to move as much information to the server and then out to the users as fast as possible. In embodiments, the processor may include a faster processor, parallelized multicore processing, smaller chips, and more powerful, deeper evaluation of biometric feedback data.

The garment 50 may comprise a wireless monitoring system that may allow for testing typically reserved for the lab. The garment 50 may comprise a processor 114 that may be wired or wirelessly connected with a plurality of respiration monitoring sites 116. Using the respiration monitoring sites 116 placed at thoracic and abdominal areas, the garment 50 may allow for respirations, heart rate, and thoracic movement to be monitored along with relevant conjoined data. The garment system 50 may allow for the integration of Bluetooth Smart enabled peripheral monitors. The wireless capabilities may also mean that this product may be updated and expanded on like any other piece of technical equipment. In embodiments, the garment 50 may comprise eight thoracic respiration monitoring sites 116 and four abdominal respiration monitoring sites 116 (both generally denoted as respiration monitoring sites 116).

A rechargeable battery 132 connected to the processor 114 may be encased in a waterproof shell that may be resistant up to 100 meters of water in embodiments. The configuration of the battery 132 may depend on the variation of the garment 50. A commercial version of the garment 50 may utilize an integrated battery 132 that may require that the garment 50 be returned to a company for a swap out battery 132 once the battery 132 has exceeded life expectancy. In embodiments, an accessible version of the garment 50 may utilize a removable battery 132 that may allow for emergency swap out, field servicing, and swaps on prolonged operations (such as in the military).

The estimated standby time for the garment 50 without kinetic influence or charge may be 10-15 days, virtually eliminating the possibility of power sapping. The garment 50 may be monitored remotely by dashboard application as well as a web interface.

The garment 50 may further comprise a plurality of strategically placed accelerometers 130. The integration of accelerometers may allow for, but is not limited to a number of characteristics. The accelerometers 130 may provide the location of the garment 50 and thus the body position of the wearer relevant to perpendicular to the ground. This may allow an evaluator to determine the activity of the garment 50 wearer (running versus biking, versus swimming, etc.). The accelerometers 130 may identify position relevant to the perpendicular in conjunction with being relevant to each other. The accelerometers 130 may further determine torso and limb movement associated with mobility. The accelerometer 130 may further determine the quality of specific movements. In embodiments, the garment 50 may comprise four accelerometers 130: a left posterior accelerometer 130, a right posterior accelerometer 130, a left anterior accelerometer 130, and a right anterior accelerometer 130. The accelerometers 130 may collect information on the movement of an individual including the direction of movement, the speed of movement, the duration in which a movement takes place, and the smoothness of the movement. This information may be provided to the processor 114 and stored on a memory in connection with the processor 114. The processor 114 may correlate the data with sample data that may represent a specific activity. This comparison may allow the garment 50 to tell what type of activity an individual is doing, how well the individual is performing an activity, and how well the individual is doing (healthwise) during the activity.

In embodiments, garment 50 may incorporate a plurality, such as four, accelerometers 130. There may be one accelerometer 130 over the posterior superior lateral aspect of the left scapula and one accelerometer 130 over the posterior superior lateral aspect of the right scapula. There may further be one accelerometer 130 placed over the left anterior superior medial aspect of the ischial crest and one accelerometer 130 placed over the right anterior superior medial aspect of the ischial crest. Each accelerometer 130 may relay information independently to the processor 114 so that the individual accelerometers' 130 positions relevant to perpendicular to the ground can be measured as well as variations to perpendicular to the ground surface. Each unit may measure its relative position, speed, and momentum respective to every other unit. This information may also be sent to the processor 114 by each individual accelerometer 130. The combined data in aggregate from the accelerometers 130 may provide a three dimensional digital view of the body in motion. In embodiments, the accelerometer component 130 of the garment 50 may include smaller accelerometers 130, more accelerometers 130, more accurate hardware, and faster aggregation at the software level.

The processor 114 may further be connected to a GPS monitor 134 that may be stacked or swapped with a WWAN monitor 134 for indoor movement tracking in a 3D space. In both instances, the purpose of the unit 134 is to determine the wearer's physical position in a real world environment. In embodiments, the ping rate for the GPS and/or the WWAN monitoring device 134 may be one second intervals (the closest to constant position streaming currently available).

The GPS component 134 of the garment 50 may utilize the most current GPS transceivers available. The GPS component 134 may be located along the spinal column over the C5. The GPS 134 may be small in size and may be low profile. The GPS 134 may utilize an integrated antenna. For military versions of the garment 50, an elongated, flexible, and flat GPS antenna may be integrated into the garment 50. The GPS component 134 of the garment 50 may be utilized to track the physical location of the body in a real-time environment. For military purposes, the garment 50 may be capable of utilizing WWAN to track a wearer through an interior environment. The WWAN integration may afford observers utilizing the app or web dashboard to track the garment's wearer in near real time on a map overlay. In embodiments, the GPS/WWAN component 134 may include smaller units, better satellite tracking, faster locking, and better transmission through dense cover.

Figure 5:
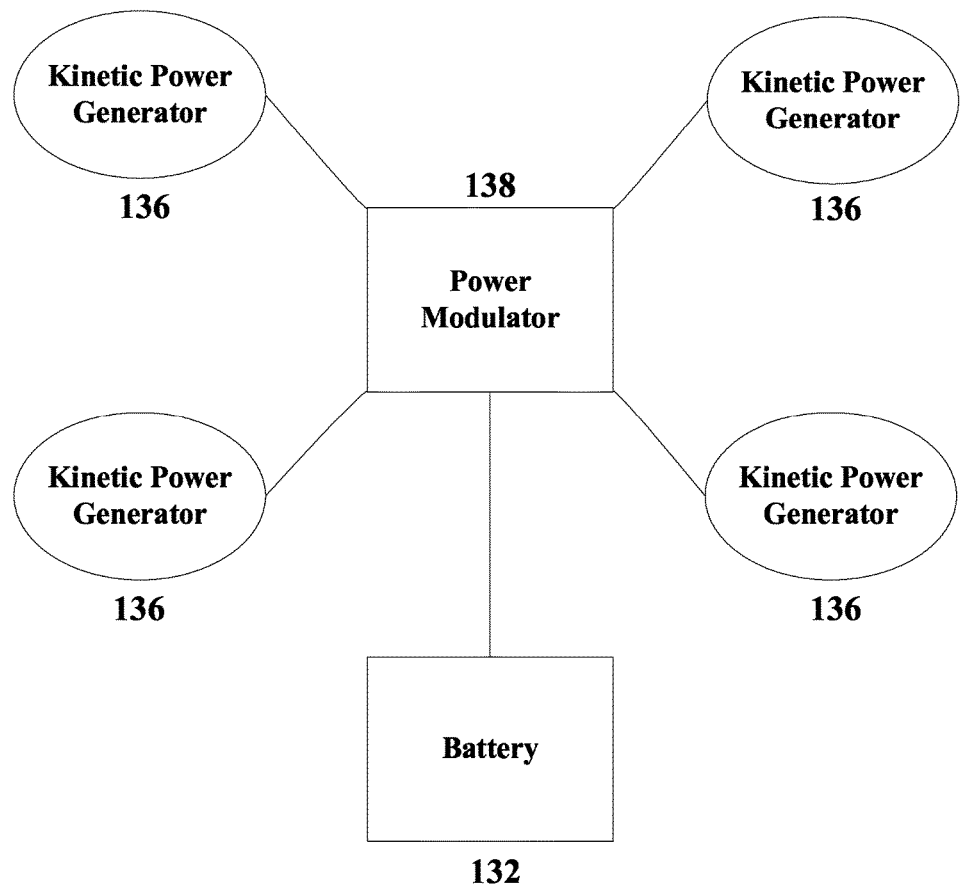
FIG. 5 displays a diagram of an embodiment of the power module setup.

FIG. 5 displays a diagram of an embodiment of the kinetic power module setup. A low frequency wireless enabled wearable utilizing at least one power generator, magnetic respiratory monitor, and onboard processor 114 may exist within the garment 50. The method of acquiring, processing, and transmitting biometric feedback data may allow for the complete physical evaluation of a wearer without being harnessed to a treadmill, spirometer, and ECG machine while isolated to a lab outside of an active real-world environment. The garment 50 may take the guess work out of live, real-world performance and stress response.

In embodiments, the garment 50 may utilize at least one integrated kinetic power generator 136 that may allow for the garment 50 to continuously charge while the wearer is in motion and may only deplete the battery 132 when the body is static. This feature may increase the battery life and decrease the requirement for charging. This may lend the garment 50 to long duration activities like combat operation scenarios such as foot patrols, Direct Action Operations, training exercises spanning multiple days in the field, and commercially viable activities such as triathlons and endurance races. In embodiments, the integrated kinetic generators 136 may be a diffuse kinetic charger.

The kinetic generator is a technology that may be integrated into the garment 50. The power generator may be a diffuse kinetic generator system that may provide multiple micro-kinetic power generators 136 that may be located throughout the garment 50 in strategic areas. The energy generated by each power generator 136 may be throttled through a power modulator 138 to trickle charge the garment's battery 132. The power modulator 138 may be capable of trickle charging the battery 132 from the charge of a single micro kinetic generator 136 or all micro-kinetic power generators 136 simultaneously. This is extremely important because in certain body positions, or during certain activities, there may be limited motion through all or some of the upper extremities and thus regions of the garment 50. The power modulator 138 may be directly wired to the battery 132 in order to provide the charge/trickle charge. In an embodiment, a micro-kinetic power generator technology may be based on the Seiko-type kinetic power generation system that has been utilized in watches since the early 80s. In embodiments, the kinetic power generators 136 may include smaller generators capable of generating more power from less movement. In embodiments, the kinetic power generators 136 may incorporate organic solar paneling woven into the garment material of the garment 50.

In embodiments, the garment 50 may comprise at least one battery 132.

Figure 6:
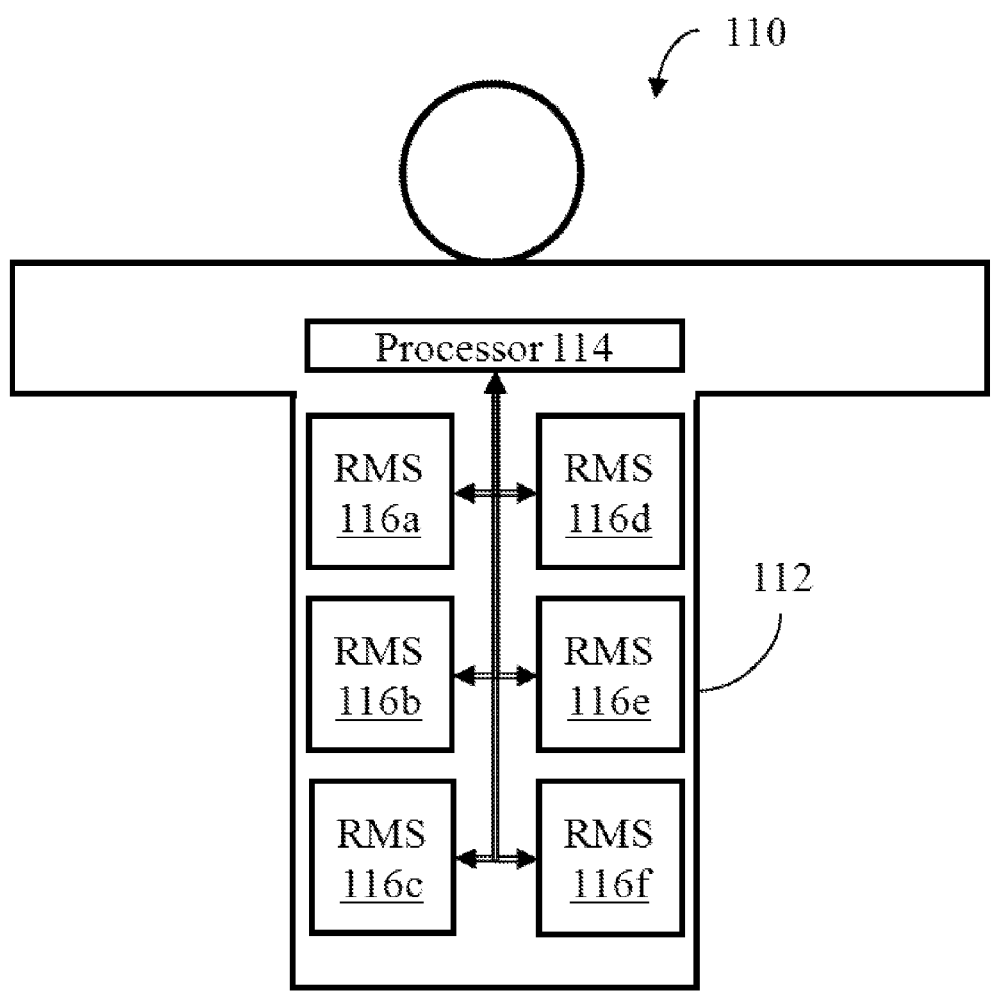
FIG. 6 illustrates a respiratory monitor sub-system 10, according to some embodiments.

FIG. 6 illustrates a respiratory monitor sub-system 10, according to some embodiments. Respiratory monitor subsystem 110 may be integrated into shirt 112 and includes processor 114 and multiple instantiations of respiration monitoring site ("RMS") 116, i.e., RMS 116*a*-116*f*. Each RMS 116 is connected to processor 114 via serial bus. During operation, each RMS 116 senses movement as described below and provides a corresponding digital output that is a function of the detected movement. According to one embodiment, each RMS 116 output is latched and scanned serially back to processor 114 where it is available for further analysis or processing. According to a different embodiment, the digital data provided by each RMS 116 may be provided to processor 114 along a parallel bus.

In embodiments, respiratory monitor sub-system 110 may not include processor 114.

Figure 7:
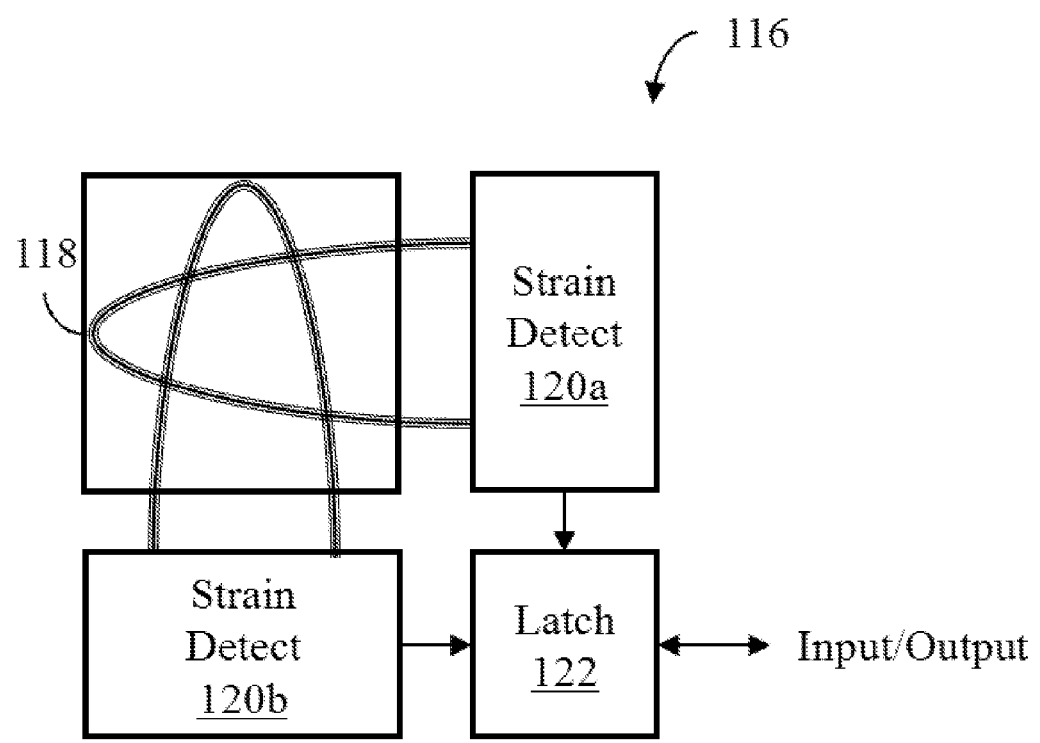
FIG. 7 illustrates a RMS according to some embodiments.

FIG. 7 illustrates an RMS 116 according to some embodiments. RMS 116 includes a conductive elastomer ("CE") panel 118, multiple instances of strain detection unit 120, i.e., strain detection unit 120*a*-120*b*, and latch 122. CE panel 118 includes at least 2 strips of material, strands, or fibers of a conductive elastomer, one substantially in the horizontal direction, and one substantially in the vertical direction. These CE panels may be integrated into the garment 112 over areas that are affected during the respiratory process; for instance, over the rib cage and upper abdomen. When inhalation and exhalation occur, the material stretches, expanding and contracting with body motion, i.e., thoracic expansion and contraction while breathing.

As is known, the resistance of the conductive elastomer fibers or threads is given as:

$$R=(p*l)/A,$$

where R represents the resistance, p represents electrical resistivity ($\Omega$m), A represents the cross sectional area in m2 and l=length of the conductor in m. According to this relation, when the area of the conductive elastomer decreases, its resistance increases. Deflection, i.e., expansion and contraction, of the conductive elastomer results in a decrease in the cross-sectional area and a concomitant change in the resistance of the conductive elastomer.

Strain detection unit 120*a* and 120*b* detect the changes in the resistance of the conductive elastomer that results from the expansion and contraction of the strands that accompany inhalation and exhalation. Latch 122 captures the results of the detection performed by strain detection unit 120 and provides the captured data to processor 114 by way of the aforementioned serial or parallel bus.

Figure 8:
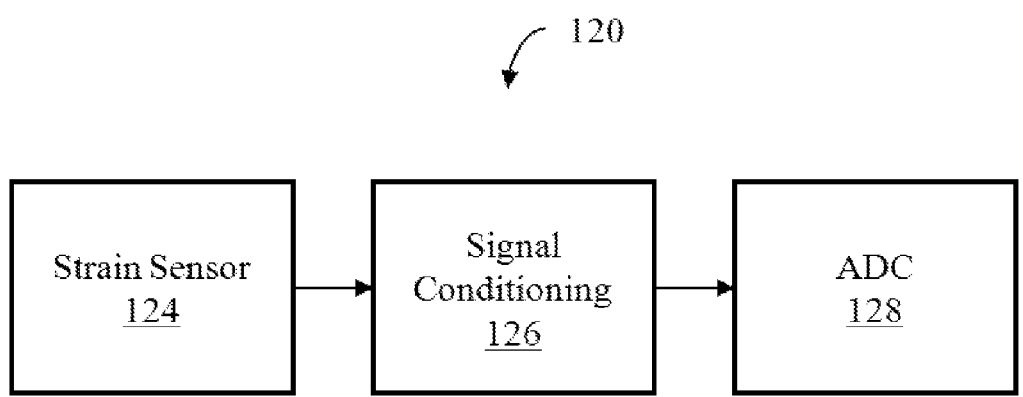
FIG. 8 illustrates a strain detection unit according to some embodiments.

FIG. 8 illustrates a strain detection unit 120 according to some embodiments. Strain detection unit 120 includes a strain sensor unit 124, signal conditioning unit 126, and analog-to-digital converter ("ADC") 128. During operation, strain sensor unit 124 detects the changes in resistance resulting from the deflection of the conductive elastomer strands due to inhalation and exhalation. The results of the strain sensor unit 124 are provided to signal conditioning unit 126, where the resulting signal or signals are, for example, amplified and any DC offset is removed. The conditioned signal is provided to ADC 128 where it signal is converted into a digital output. ADC 128 may be a simple 1-bit ADC, a more complex 24-bit ADC, or something in between, depending upon the application and the needs of the system.

Figure 9:
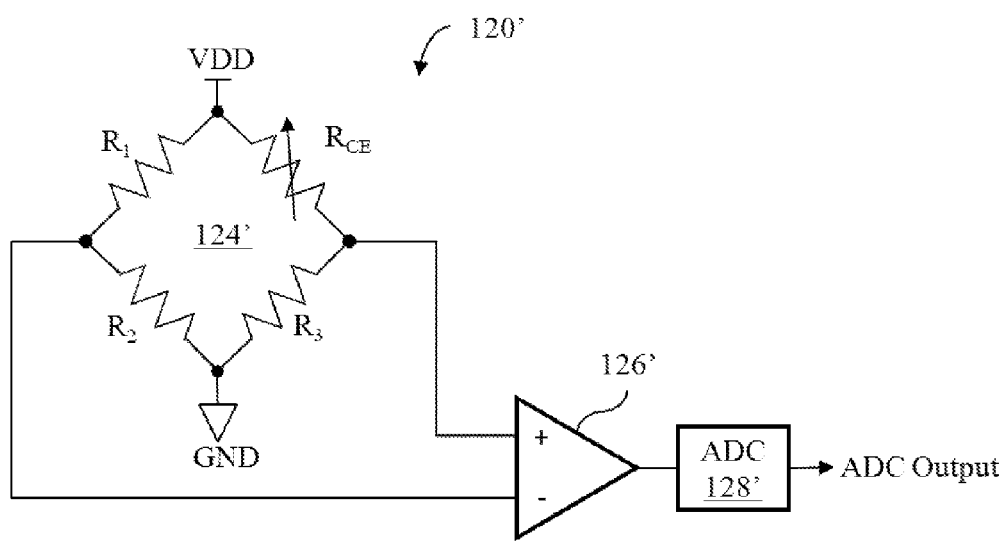
FIG. 9 illustrates a strain detection unit according to a different embodiment.

FIG. 9 illustrates a strain detection unit 120' according to a different embodiment. In this embodiment, strain detection unit 120' includes Wheatstone bridge 124', amplifier 126', and ADC 128'. Wheatstone bridge 124', as is known, is often used to accurately measure small changes in resistance of a strained medium, converting the changes in resistance into a voltage that can be amplified by amplifier 126' and converted to a digital output by ADC 128'. Wheatstone bridge 24' includes 4 resistors R1, R2, R3, and RCE, where RCE is the resistance of the conductive elastomer. When all four resistors in Wheatstone bridge 124' are equal, the bridge is perfectly balanced and the output voltage is equal to zero. But when any one or more of the resistors change value by only a fractional amount, the bridge produces a measurable voltage. The output voltage of the Wheatstone bridge 124' is given by:

$$V_{out}=VDD((R2/(R1+R2))-(R3/(RCE+R3)))$$

Thus, when the resistance of the conductive elastomer, illustrated here as RCE, changes, the output voltage provided to amplifier 126' reflects that change as a change in voltage which is then conditioned and amplified by amplifier 126'. The amplified signal is then converted to a digital output by ADC 128'. As before, ADC 128' may be a simple 1-bit ADC, a more complex 24-bit ADC, or something in between, depending upon the application and the needs of the system.

Figure 10:
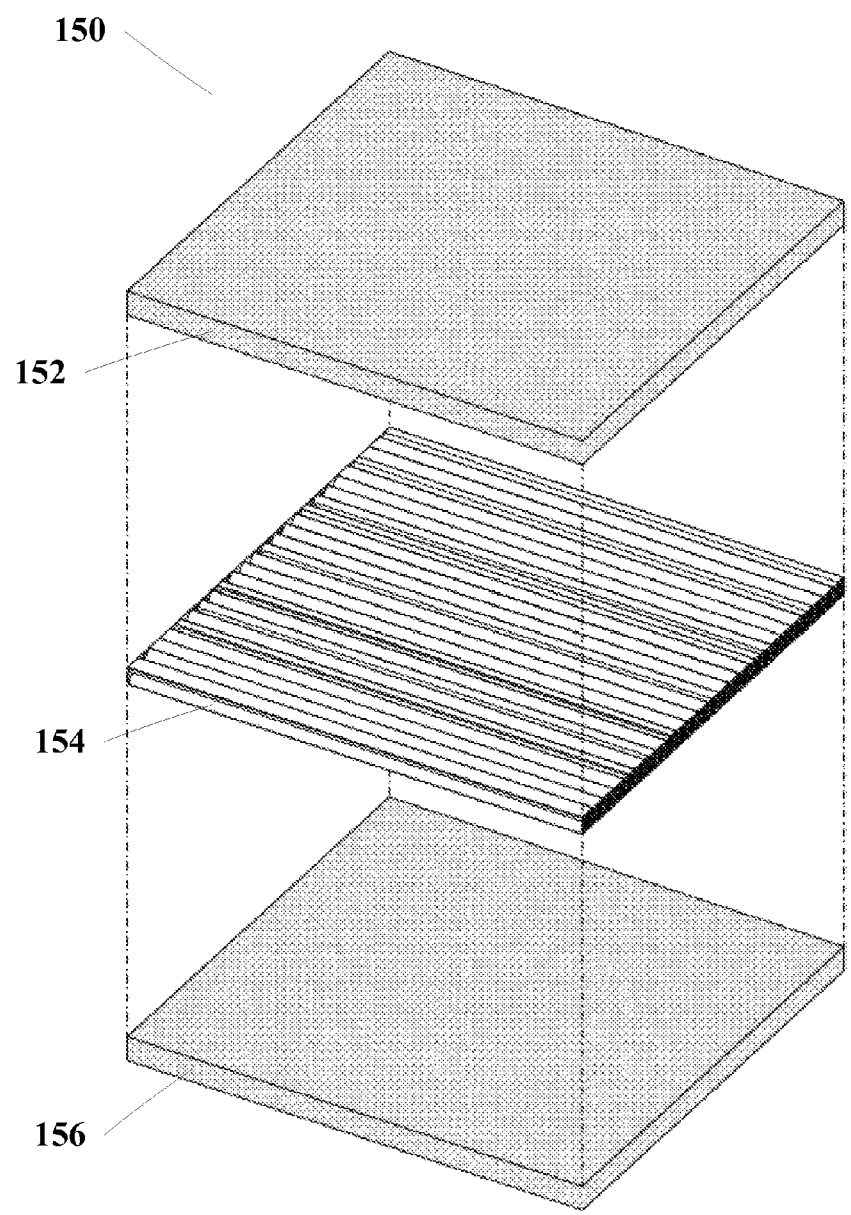
FIG. 10 displays a side layer view of a multi-layer conductive fabric utilized by a garment in accordance with embodiments.

FIG. 10 displays a side layer view of a multi-layer elastic conductive fabric 150 utilized by a garment 50 in accordance with embodiments. The fabric 150 may comprise a top layer 152, a bottom layer 156, and a crosslinked midsection 154. In embodiments, the bottom layer 156 may comprise a rubberized conducive material, such as, but not limited to a metal rubber. A metal rubber may provide an ideal set of properties that may include elasticity and conductivity. When an individual is wearing the garment 50, the bottom layer 156 may exist adjacent the individual's skin. The bottom layer 156 may receive a natural current from the individual's skin that may be transmitted throughout the bottom layer 156. In embodiments, this natural current may be measured by one or more RMS 116 and may output data that may be analyzed to show how an individual is positioned or is breathing. In embodiments, a current from a component of the garment 50 may provide a current that may be supplied to the bottom layer 156 and one or more RMS 116. In embodiments, the current supplying component may be battery 132.

The midsection 154 may comprise a woven textile including insulative fibers. It is important to note that the insulative fibers of the woven textile may be adjacent the bottom layer 156 so that the bottom layer 156 may carry a charge from one point to another without the midsection 154 interfering with the current passed through the bottom layer 156. The top layer 152 may comprise an elastic fabric such as, but not limited to spandex and lycra. In embodiments, the midsection 154 may be adhered to the top and bottom layers 152,156 via an adhesive polymer. In embodiments, the woven textile of the midsection 154 may be woven to at least one of the top and bottom layers 152,156. In embodiments, the elastic conductive polymer may exhibit characteristics similar to a metal rubber.

Figure 11:
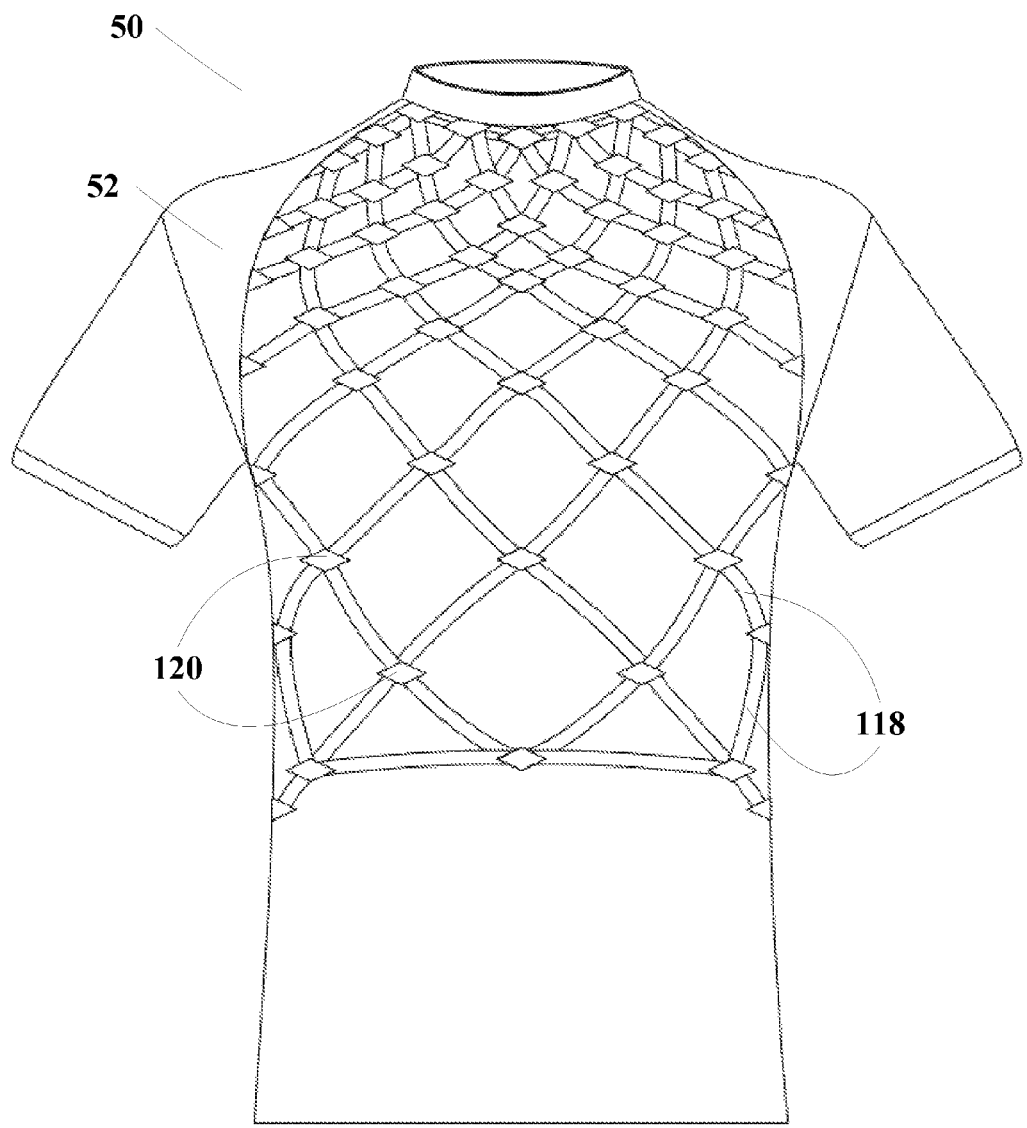
FIG. 11 displays a front view of a respiratory monitor system engrained within a garment in accordance with embodiments.

FIG. 11 displays a front view of a respiratory monitoring system engrained within a garment 50 in accordance with embodiments. As shown in FIG. 11, the multi-layer elastic conductive fabric 150 may comprise a definite width that may be confined within a length from a first detection unit 120 to a second detection unit 120. In embodiments such as that shown in FIG. 11, the multi-layer elastic conductive fabric 150 may alternatively be designated as "panel strips". A plurality of panel strips may make up a framework splayed across the garment 50 in diagonal patterns to provide conductivity to a plurality of detection units 120 found on a large portion of the garment 50. These panel strips may be woven and/or stitched to the garment 50 itself. At each contact point/overlap, a detection unit 120 may exist that may create a data packet on the current being passed at that specific monitor. The data packet may include a time at which a current is measured. The detection units 120 may then send the information to either a processor 114 on the garment 50 or an external processor that may store and analyze the data packets received using either a wired or wireless connection (such as those mentioned herein). Using one or more algorithms, the processor 114 may output breathing information on an individual wearing the garment 50.

Figure 12:
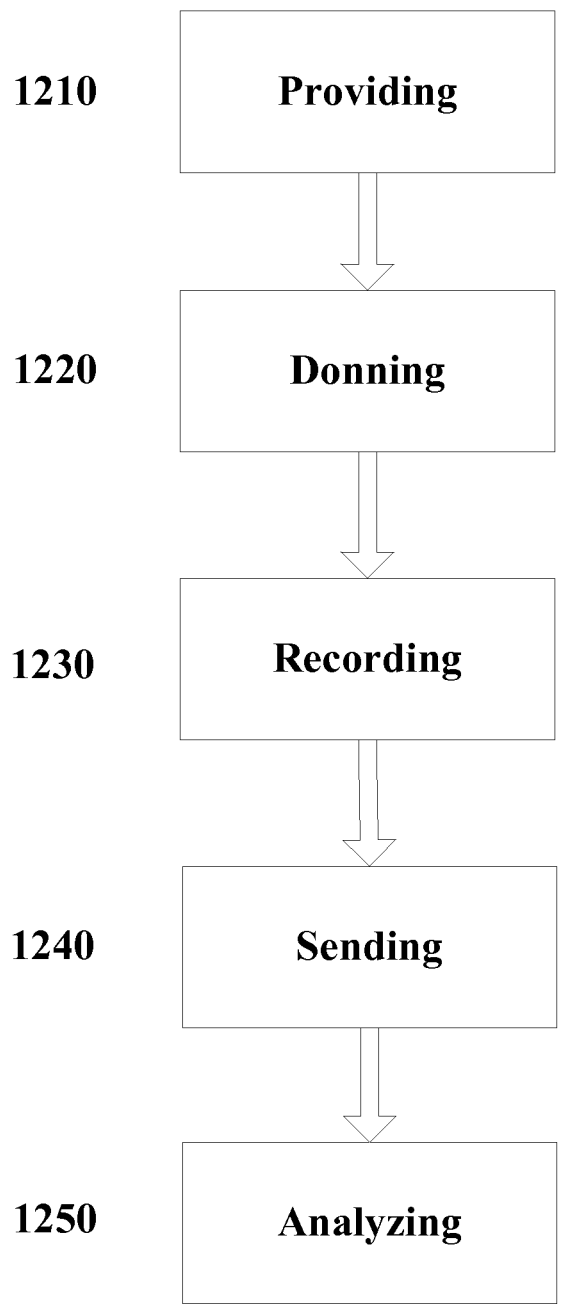
FIG. 12 displays a method for monitoring body functions in accordance with embodiments.

FIG. 12 displays a method 1200 for monitoring body functions in accordance with embodiments. Method 1200 may measure functions such as, but are not limited to inspiration, expiration, skeletal positional quality, and volume of respiration. Method 1200 may utilize any of the aforementioned embodiments of a garment 50 including a respiratory monitor matrix and detection units 120. Method 1200 may be utilized in conjunction with the physical movements of the respiratory process. Method 1200 may include providing 1210 a garment 50 to an individual. The user may don 1220 the garment 50 and may breathe (perform inspiration and expiration) while wearing the garment 50, causing the multi-layer elastic conductive fabric 150 of the garment 50 to elongate and the conductive fibers in the material to become uniformly thinner. As the conductive fibers become thinner, the resistance along the conductive fibers increases. Because of the increased resistance, the transmission time of the electrical signal across the fabric increases. These transmission times may be recorded 1230 by detection units 120 placed within the garment 50. The material may be incorporated into the garment 50 so that all expansion of fibers is along a linear plane. The recordation of times may then be included in information packets sent 1240 to a processor 114 for further analysis 1250.

Figure 13A:
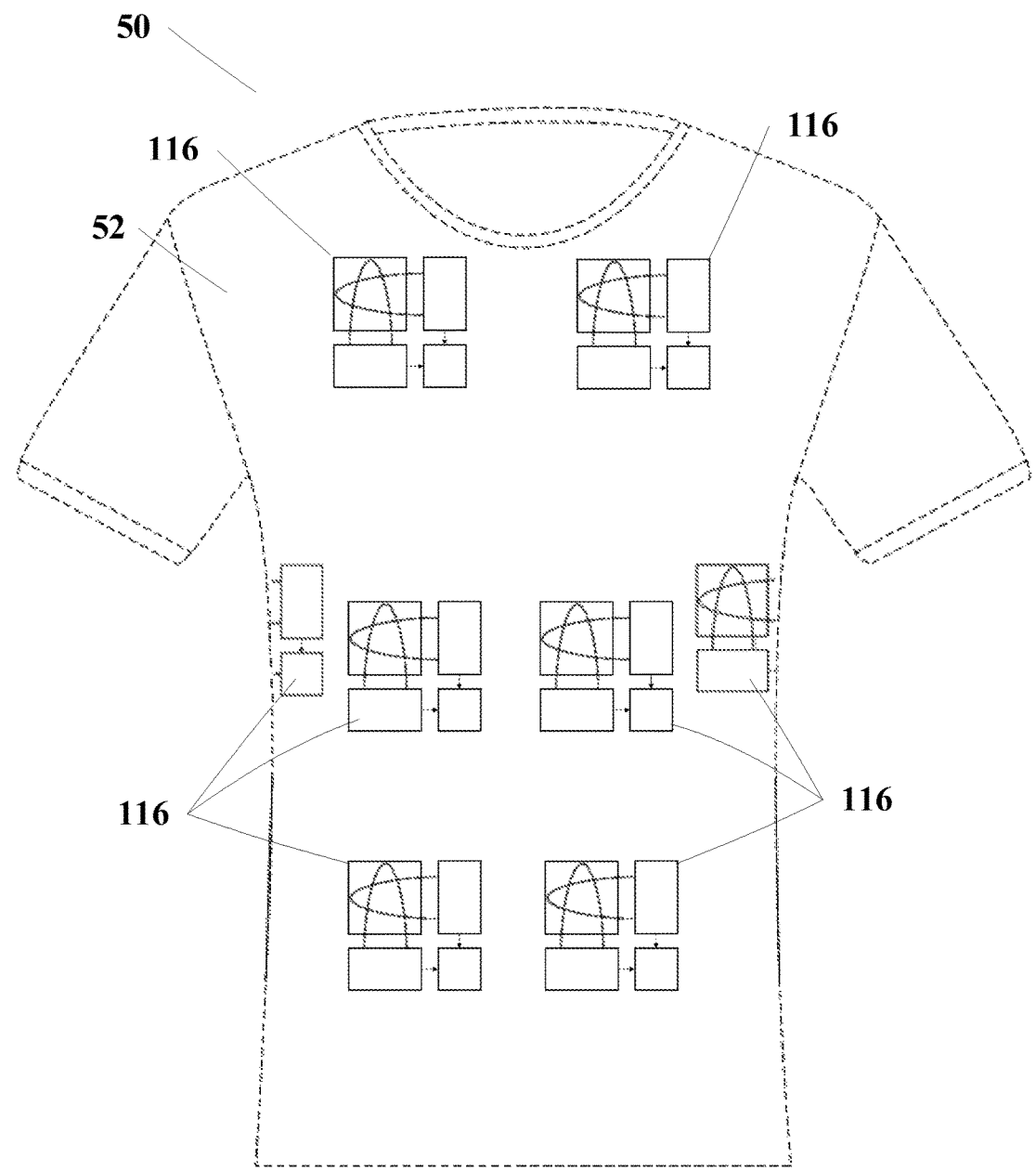
FIGS. 13A and 13B depict an alternative embodiment of a garment including a plurality of respiratory monitor sub-systems located on the anterior and the posterior of the garment.
Figure 13B:
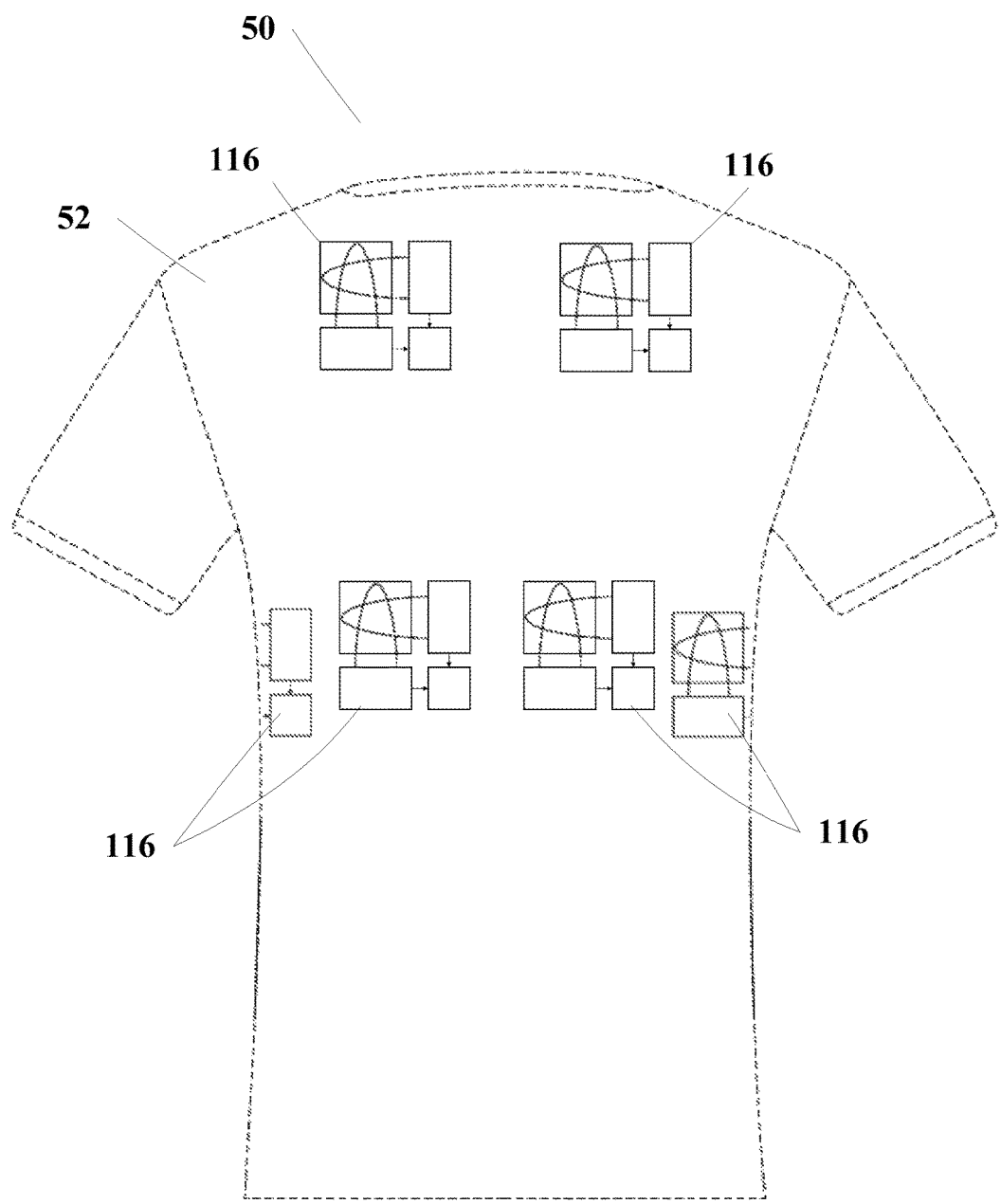

FIGS. 13A and 13B depict an alternative embodiment of a garment 50 including a plurality of RMSs 116 located on the anterior and the posterior of the garment 50. The RMSs 116 may be integrally placed to provide sufficient monitoring of an individual's bodily movements, functions, and/or positioning. The garment 50 may comprise six RMSs 116 located on the anterior portion of the garment 50, four RMSs 116 located on the posterior portion of the garment 50, and two RMSs 116 located right below the armpit portions of the garment 50.

Figure 14A:
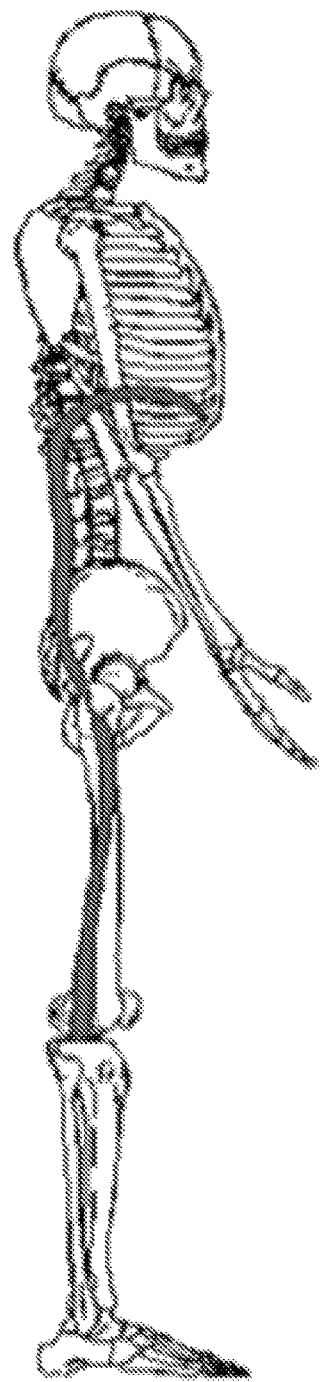
FIGS. 14A and 14B depict alternative views of a skeleton each comprising varying posture traits in accordance with embodiments.
Figure 14B:
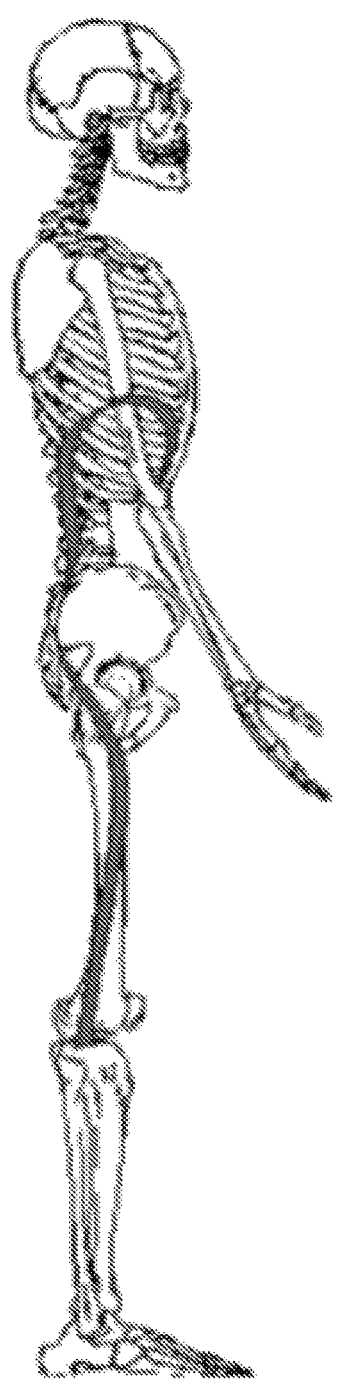

FIGS. 14A and 14B depict alternative views of a skeleton each comprising varying posture traits in accordance with embodiments. These posture traits may be analyzed using the RMSs 116 found on the garment 50. The detection units 120 utilized in the RMSs 116 are not just quantitative (like how rapidly someone is breathing or how fast their heart is beating), but are also qualitative. The garment 50 may allow a window into how effectively an individual is breathing, what subtle positional factors in their spine and ribcage exist, and what state their autonomic nervous system is in as they train (rest and recover).

The autonomic nervous system (ANS) regulates most of the body's crucial systems like digestive, cardiac, immune and lymphatic systems. This may be achieved via a balanced relationship between two sub-systems, the parasympathetic or "rest and digest" system (PNS) and the sympathetic "fight or flight" system (SNS).

Studies on elite performers ranging from Navy SEALs to students taking college entrance exams show that the top performers have the best variance in their nervous systems and are able to baseline most effectively in a restful, parasympathetic state when at rest.

These elite performers are able to spike strongly and immediately into a powerful sympathetic response when needed, and then abruptly drop back into recovery mode between either sets of a tennis match, jumping out of an airplane, or while at home over the weekend. Their heart rates dip more at night during sleep than their lower-performing counterparts, and they hit harder with a more robust "engage threat" response when called upon. Top performers have greater biological power because they only put their foot on the gas at the precise times when it's necessary. Underperformers are essentially working with one foot on the gas and the other on the brake at all times, neither hitting top speed nor slowing down and taking stress off the engine. Variability is availability.

Much of this analysis comes down to breathing and the interplay between respiratory patterns, heart rate, the autonomic nervous system, and the positioning of the spine and ribcage. The garment 50 may allow near real-time monitoring and dynamic adjustment of all of the above.

Breathing is generally misunderstood, predictably inefficient even in well-trained athletes and difficult to monitor without the disclosed garment 50. Breathing is a direct input into the autonomic nervous system (ANS) and drives positioning of the thorax, which is not only crucial for effective performance and the avoidance of injuries, but again directly affects the ANS.

The body has inherent physical asymmetries. For example, the liver is located on the right of the torso, with the heart shifted towards the left side of the chest. The liver's position offsets the diaphragm on the right, tenting it upward, while the diaphragm on the left is unaffected. The lungs have two lobes on the left and three on the right. These and other asymmetries drive predictable positional imbalances throughout the body. Many of these are tied into respiration.

As a result, not only does the spine rotate in a predictable and injurious fashion, people tend to baseline in spinal extension, which induces a state of chronic sympathetic tone, reduced ANS variability and a host of physiological issues, partially due to activation of sympathetic spinal ganglia. This has profound impacts on everything from physical performance to sleep quality and stress management.

A combination of these asymmetries, the postural influences and chronic, mild stress-state of modern life and other factors produce predictable and measurable changes in breathing, spinal and rib positioning and autonomic function. Being able to monitor and adjust these factors dynamically during training based on near real-time feedback is immensely valuable, and is where the disclosed garment 50 may be uniquely capable.

The garment 50 may allow for monitoring of the asymmetric, multi-planar (transverse, sagittal and frontal) movement of the abdomen, spine and thorax during respiration and movement. It also provides a direct window into cardiac workload and autonomic balance via heart rate and heart rate variability monitoring. This provides a valuable form of training feedback for everything from intense military training scenarios to strength and endurance training to meditative biofeedback exercises.

By utilizing embodiments of the garment 50 with one or more sub-systems, the garment 50 may recognize the position of certain body parts that may correlate with a specific posture of an individual's body. For example, the garment 50 may categorize an individual's spinal position as found in either FIG. 14A or FIG. 14B. This may be determined by running a current through a plurality of RMSs 116 and measuring the time lapsed from one sensor to another. This time measurement may be compared with other time measurements (via a processor) recorded from other garments 50 utilized by other individuals with varying spinal positions. Information may further be supplied about how an individual may alter their spinal position if desired via the information gathered on other individual's varying spinal positions. Body parts that may be analyzed may include, but are not limited to the chest, the spine, and the pelvis.

The disclosure may provide an alternative garment system 50 for providing data. The system 50 may comprise a garment body 52 comprising an anterior portion, a posterior portion, and a plurality of yarns arranged in at least one of a woven pattern and a knit pattern. The garment body 52 may further comprise the following components: a processor 114, a memory, a battery unit 132, a respiratory monitor sub-system 110 including a plurality of respiratory monitoring sites 116, a plurality of kinetic generators 136 wired to a power modulator 138 connected to the battery 114, a GPS monitor 134, a plurality of accelerometers 130, and a data analysis module comprising a second wireless receiver and a wireless transmitter.

In embodiments, the module may be capable of receiving data procured from at least one of the processor 114, the respiratory monitor sub-system 110, the GPS monitor 134, and the plurality of accelerometers 130.

In embodiments, at least one of the plurality of accelerometers 130 may be wired to the processor 114.

In embodiments, the processor 114, the GPS monitor 134, and the plurality of accelerometers 130 may each comprise at least one of a wireless receiver and a wireless transmitter. In embodiments, each of the plurality of respiratory monitoring sites 116 may be affixed to at least one other of the plurality of respiratory monitoring sites 116 via conductive flexible fibers.

In embodiments, the components may be configured in a skeletal substructure, wherein: the processor 114 and memory may be housed as a unit affixed to the posterior portion of the garment body 52, the battery unit 132 may be affixed to the posterior portion of the garment body 52, the plurality of respiratory monitoring sites 116 may be affixed to the anterior portion of the garment body 52 and the posterior portion of the garment body 52, at least one of the plurality of kinetic generators 136 may be affixed to the anterior portion of the garment body 52 and the posterior portion of the garment body 52, the GPS monitor 134 may be affixed to the posterior portion of the garment body 52, and at least one of the plurality of accelerometers 130 may be affixed to the anterior portion of the garment body 52 and the posterior portion of the garment body 52.

In embodiments, the garment system 50 may comprise a form-fitting fabric comprising an open interior defining a torso.

In embodiments, the form-fitting fabric may comprise three layers. Each of the three layers may separately comprise one of a conductive elastic fabric, an insulative fabric, and an elastic fabric.

In embodiments, the layer comprising the conductive elastic fabric may be adjacent the open interior. The conductive elastic fabric may essentially be adjacent an individual's skin when an individual is wearing an embodiment of garment 50.

In embodiments, the battery unit 132 may be housed in a waterproof battery shell. In embodiments, the battery 132 may be rechargeable. In embodiments, at least one of the plurality of accelerometers may comprise a heart rate monitor.

In embodiments, the garment body 52 may further comprise a magnetic monitoring system comprising at least one magnetic monitoring unit In embodiments, the magnetic monitoring unit may comprise a housing, a magnet static within the housing, a magnet mobile within the housing, and a magnetometer comprising a sensor positioned within the housing. The sensor may measure the force within the magnetic field created by the two magnets at different times, such as when the mobile magnet is close to the static magnet and when the mobile magnet is far away from the static magnet. These distances between the magnets may occur at a time when an individual is breathing (chest compressions may change the distance of the magnets when the magnetic monitoring system is incorporated into a garment 50 in the chest region). In order to keep both magnets from moving in relation to the garment 50 when a person breathes, one of the magnets may be affixed to the garment 50 and not the housing while the other magnet may be affixed to the housing but not the garment 50. In embodiments, affixing of one of the magnets to the garment 50 may be carried out using a single magnet housing affixable to the garment that may penetrate the housing (of both magnets) that may be movable with the magnet in which the single magnet housing is encompassing.

Figure 15:
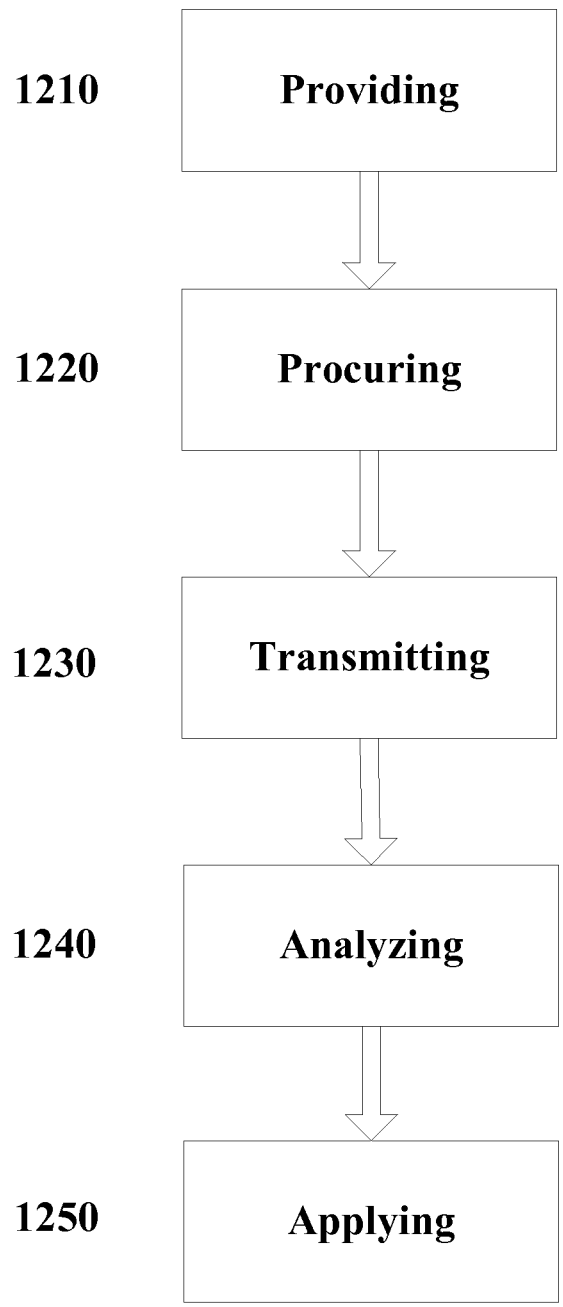
FIG. 15 displays an alternative embodiment of a method for collecting data in accordance with embodiments.

FIG. 15 displays an alternative embodiment of a method 1500 for collecting data in accordance with embodiments. Method 1500 may utilize any embodiment of a garment system 50 that is described above in paragraphs [0095] to [00104]. The method 1500 may comprise providing 1210 a garment system 50. Data may be procured 1220 via at least one of the processors 114 of the garment system 50, the respiratory monitor sub-system 110, the GPS monitor 134, and at least one of the plurality of accelerometers 130. The procured data may then be transmitted 1230 to at least one of the processor 114 and the data analysis module. The procured data may be analyzed 1240 via at least one of the processor 114 and the data analysis module. An algorithm may then be applied 1250 to the procured data via at least one of the processor 114 and the data analysis module in order to provide a processed output. The processed output may include biometric information associated with an individual wearing a garment 50.

Figure 16:
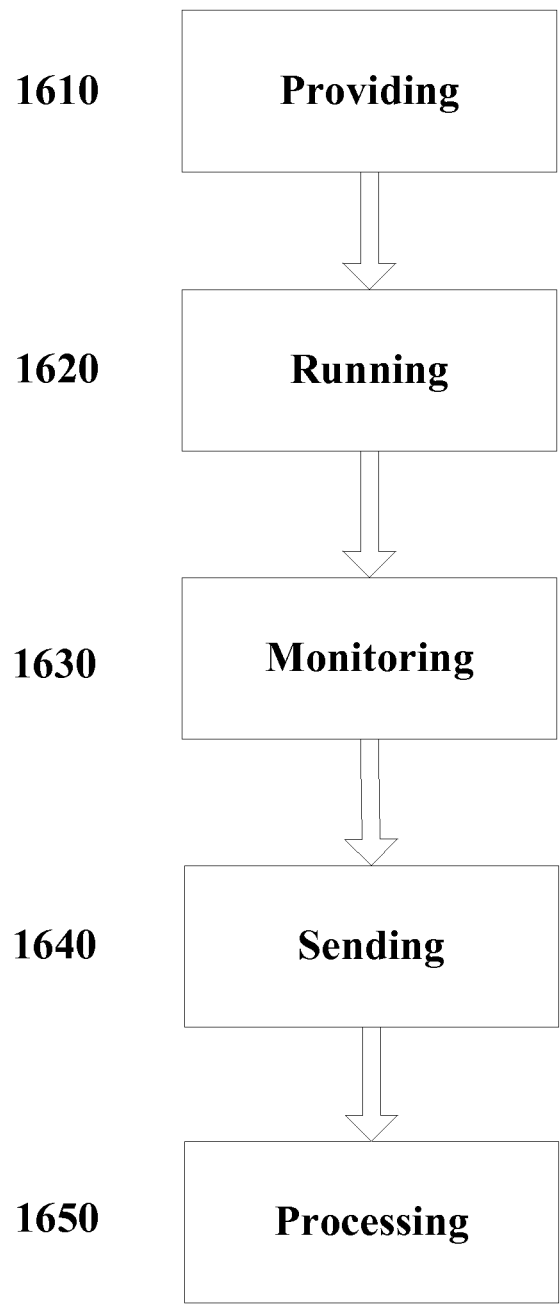
FIG. 16 displays a method for monitoring breathing in accordance with embodiments.

FIG. 16 displays a method 1600 for monitoring breathing in accordance with embodiments. Method 1600 may comprise providing 1610 a garment system 50. The garment system 50 may comprise a garment body 52 comprising a plurality of yarns arranged in at least one of a woven pattern and a knit pattern. The garment 50 may further comprise a respiratory monitor sub-system 110 comprising a plurality of respiratory monitoring sites 116. Each of the plurality of respiratory monitoring sites 116 may be affixed to at least one other of the plurality of respiratory monitoring sites 116 via conductive flexible fibers. In embodiments, the garment 50 may comprise any of the aforementioned features.

Method 1600 may further comprise running 1620 a current through at least some of the conductive flexible fibers and at least two of the plurality of respiratory monitoring sites 116, wherein the at least some of the conductive flexible fibers are in a nonlinear position in response to an applied force.

Method 1600 may further comprise monitoring 1630 and recording current information at the at least two of the plurality of respiratory monitoring sites 116. In embodiments, the current information may include assigning a time stamp to the current at the point in time the current is received by each of the at least two of the plurality of respiratory monitoring sites 116.

Method 1600 may further comprise sending 1640, via at least one of a wired network and a wireless network, the current information to a processor 114. In embodiments, the processor may comprise at least one algorithm.

Method 1600 may further comprise processing 1650, via the at least one algorithm, the current information to provide a processed output.

In embodiments, operating systems utilized by any part of the garment 50 system may include, but is not limited to: iOS 5 and later, Windows Phone 8.1, Windows 8, Android 4.3 and later, BlackBerry 10, Linux 3.4 and later through BlueZ 5.0, and Unison OS 5.2.

In embodiments, any of the electronic components of the garment 50 may comprise a waterproof nano-coating adhered to the exterior of the electronic components. The coating may allow for the components to function properly when the garment 50 is exposed to a wet environment that may include sweat and/or water.

In embodiments, wiring connecting two or more electronic components found in a garment 50 may be contained within a multi-layered fabric construction. In embodiments, the wiring may be partially engrained within seams in the garment 50. In embodiments, the wiring may comprise conductive fibers. The conductive fibers may be in the form of one or more yarns woven or knit with other fibers. In order to provide the efficient transfer of power or data, the yarns may be coated with an insulative polymer.

In embodiments, the garment system 50 may be capable of monitoring multiple biometric responses such as, but not limited to: skin temperature, core temperature, respirations, heart rate, predicted tidal volume, chest wall movement, abdominal movement in conjunction with inspiration, abdominal movement in conjunction with expiration, HRR (heart rate reserve), HRV (heart rate variability), body position relevant to perpendicular, shoulder position relevant to hip position, general body posture, up time, down time, and malfunctions.

In embodiments, the garment system 50 may be capable of monitoring multiple biometric peripheral processes through Bluetooth Smart or similar. These biometric peripheral processes include, but are not limited to: DTR, eye movement, eye position, reflex velocity, visual tracking, visual focal points, tactile response, and skin conductivity.

In certain embodiments, the garment system 50 may be a garment other than a shirt. These other garments may include any of the structures and/or functionalities found in the disclosure.

In embodiments, fabric within the garment structure 50 may comprise a twill weave. The twill weave may provide a better form fitting structure to the body by allowing the garment 50 to succumb easier to flexing or folding to match the curves of a body.

For the purposes of this disclosure, the term "garment" may refer to a belt in embodiments.

For the purpose of this disclosure, the terms "garment", "garment system", and "system 50" may be synonymous.

For the purposes of this disclosure, the terms "respiration/skeletal position monitors", "RMSs", and "respiration monitoring sites" may be synonymous.

For the purposes of this disclosure, the terms "respiration monitor sub-system" and "respiration monitoring sub-system" may be synonymous.

For the purposes of this disclosure, the terms "battery unit" and "battery" may be synonymous.

The invention claimed is:

1. A garment system for providing data comprising:
   a garment body comprising an anterior portion, a posterior portion, and a plurality of yarns arranged in at least one of a woven pattern and a knit pattern, the garment body further comprising the following components:
   a processor;
   a memory;
   a battery unit;
   a respiratory monitor sub-system comprising a plurality of respiratory monitoring sites, each of the plurality of respiratory monitoring sites affixed to at least one other of the plurality of respiratory monitoring sites via conductive flexible fibers;
   a plurality of kinetic generators wired to a power modulator connected to the battery;
   a GPS monitor; and
   a plurality of accelerometers, at least one of the plurality of accelerometers wired to the processor;

the processor, the GPS monitor, and the plurality of accelerometers each comprising at least one of a wireless receiver and a wireless transmitter; and a data analysis module comprising a second wireless receiver and a wireless transmitter, the module capable of receiving data procured from at least one of the processor, the respiratory monitor sub-system, the GPS monitor, and the plurality of accelerometers.

2. The system of claim 1, the components configured in a skeletal substructure, the processor and memory housed as a unit affixed to the posterior portion of the garment body,
the battery unit affixed to the posterior portion of the garment body,
the plurality of respiratory monitoring sites affixed to the anterior portion of the garment body and the posterior portion of the garment body,
at least one of the plurality of kinetic generators affixed to the anterior portion of the garment body and the posterior portion of the garment body,
the GPS monitor affixed to the posterior portion of the garment body, and
at least one of the plurality of accelerometers affixed to the anterior portion of the garment body and the posterior portion of the garment body.

3. The system of claim 1, the garment system comprising a form-fitting fabric comprising an open interior defining a torso.

4. The system of claim 3, the form-fitting fabric comprising three layers, each of the three layers separately comprising one of a conductive elastic fabric, an insulative fabric, and an elastic fabric.

5. The system of claim 4, the layer comprising the conductive elastic fabric adjacent the open interior.

6. The system of claim 1, the battery unit housed in a waterproof battery shell.

7. The system of claim 1, the battery unit being rechargeable.

8. The system of claim 1, at least one of the plurality of accelerometers comprising a heart rate monitor.

9. The system of claim 1, the garment body further comprising a magnetic monitoring system comprising at least one magnetic monitoring unit, the magnetic monitoring unit comprising:
a housing;
a magnet static within the housing;
a magnet mobile within the housing; and
a magnetometer comprising a sensor positioned within the housing.

10. A method for collecting data comprising:
providing a garment system, the garment system comprising:
a processor;
a memory;
a battery unit;
a respiratory monitor sub-system comprising a plurality of respiratory monitoring sites, each of the plurality of respiratory monitoring sites affixed to at least one other of the plurality of respiratory monitoring sites via conductive flexible fibers;
a plurality of kinetic generators wired to a power modulator connected to the battery;
a GPS monitor; and
a plurality of accelerometers, at least one of the plurality of accelerometers wired to the processor;
the processor, the GPS monitor, and the plurality of accelerometers each comprising at least one of a wireless receiver and a wireless transmitter; and
a data analysis module comprising a second wireless receiver and a wireless transmitter, the module capable of receiving data procured from at least one of the processor, the respiratory monitor sub-system, the GPS monitor, and the plurality of accelerometers;
procuring data via at least one of the processor, the respiratory monitor sub-system, the GPS monitor, and at least one of the plurality of accelerometers;
transmitting, to at least one of the processor and the data analysis module, the procured data;
analyzing, via the at least one of the processor and the data analysis module, the procured data; and
applying, via the at least one of the processor and the data analysis module, an algorithm to the procured data to provide a processed output.

11. The method of claim 10, the processor, the memory, the battery unit, the plurality of respiratory monitoring sites, the plurality of kinetic generators, the GPS monitor, and the plurality of accelerometers configured in a skeletal substructure, the processor and memory housed as a unit affixed to the posterior portion of the garment body,
the battery unit affixed to the posterior portion of the garment body,
the plurality of respiratory monitoring sites affixed to the anterior portion of the garment body and the posterior portion of the garment body,
at least one of the plurality of kinetic generators affixed to the anterior portion of the garment body and the posterior portion of the garment body,
the GPS monitor affixed to the posterior portion of the garment body, and
at least one of the plurality of accelerometers affixed to the anterior portion of the garment body and the posterior portion of the garment body.

12. The method of claim 10, the garment system comprising a form-fitting fabric comprising an open interior defining a torso.

13. The method of claim 12, the form-fitting fabric comprising three layers, each of the three layers separately comprising one of a conductive elastic fabric, an insulative fabric, and an elastic fabric.

14. The method of claim 13, the layer comprising the conductive elastic fabric adjacent the open interior.

15. The method of claim 10, the battery unit housed in a waterproof battery shell.

16. The method of claim 10, the battery unit being rechargeable.

17. The method of claim 10, at least one of the plurality of accelerometers comprising a heart rate monitor.

18. The method of claim 10, the garment body further comprising a magnetic monitoring system comprising at least one magnetic monitoring unit, the magnetic monitoring unit comprising:
a housing;
a magnet static within the housing;
a magnet mobile within the housing; and
a magnetometer comprising a sensor positioned within the housing.

19. A method for monitoring breathing comprising:
providing a garment system, the garment system comprising:

a garment body comprising a plurality of yarns arranged in at least one of a woven pattern and a knit pattern, and a respiratory monitor sub-system comprising a plurality of respiratory monitoring sites, each of the plurality of respiratory monitoring sites affixed to at least one other of the plurality of respiratory monitoring sites via conductive flexible fibers;

running a current through at least some of the conductive flexible fibers and at least two of the plurality of respiratory monitoring sites, the at least some of the conductive flexible fibers in a nonlinear position in response to an applied force;

monitoring and recording current information at the at least two of the plurality of respiratory monitoring sites, the current information including assigning a time stamp to the current at the point in time the current is received by each of the at least two of the plurality of respiratory monitoring sites;

sending, via at least one of a wired network and a wireless network, the current information to a processor, the processor comprising at least one algorithm; and processing, via the at least one algorithm, the current information to provide a processed output.

* * * * *